(12) United States Patent
Fraunhofer et al.

(10) Patent No.: US 10,183,117 B2
(45) Date of Patent: Jan. 22, 2019

(54) WEARABLE AUTOMATIC INJECTION SYSTEM AND APPARATUS

(71) Applicant: AbbVie Inc., North Chicago, IL (US)

(72) Inventors: Wolfgang Fraunhofer, Gurnee, IL (US); James Cameron, Portland, OR (US); Linas P. Laurusonis, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 56 days.

(21) Appl. No.: 14/885,916

(22) Filed: Oct. 16, 2015

(65) Prior Publication Data

US 2016/0106921 A1    Apr. 21, 2016

Related U.S. Application Data

(60) Provisional application No. 62/065,647, filed on Oct. 18, 2014.

(51) Int. Cl.
*A61M 5/20* (2006.01)
*A61M 5/24* (2006.01)
*A61M 5/19* (2006.01)
*A61M 5/142* (2006.01)

(52) U.S. Cl.
CPC ...... *A61M 5/2066* (2013.01); *A61M 5/14244* (2013.01); *A61M 5/14248* (2013.01);
(Continued)

(58) Field of Classification Search
CPC ............ A61M 5/2066; A61M 5/14244; A61M 5/14248; A61M 2005/206; A61M 5/19;
(Continued)

(56) References Cited

U.S. PATENT DOCUMENTS 4,059,109 A    11/1977    Tischlinger
5,941,867 A *    8/1999    Kao .................. A61J 1/067
                                                    604/403

(Continued)

FOREIGN PATENT DOCUMENTS

EP    2058020 A2    5/2009
WO    88/02265 A1    4/1988
(Continued)

OTHER PUBLICATIONS

International Search Report and Written Opinion issued in International Application No. PCT/US2015/056081, dated Jan. 28, 2016.
(Continued)

*Primary Examiner* — Theodore Stigell
*Assistant Examiner* — Hong-Van Trinh
(74) *Attorney, Agent, or Firm* — McCarter & English, LLP; David R. Burns

(57) ABSTRACT

A wearable automatic injection device is provided for administering a final medicament to a patient. The wearable automatic injection device comprises a housing, an injection assembly for injecting the patient with the final medicament, a container holding a bulk intermediate medicament and a diluent to be mixed to form the medicament, and a mixing mechanism for mixing the bulk intermediate medicament and the diluent in the container to form the final medicament prior. A system for administering a final medicament to a patient is also provided. The system comprises a container, a mixing mechanism for mixing a bulk intermediate medicament and a diluent in the container to form the final medicament, and a wearable automatic injection device configured to receive the container.

5 Claims, 20 Drawing Sheets

(52) U.S. Cl.
CPC .............. *A61M 5/19* (2013.01); *A61M 5/2448* (2013.01); *A61M 2005/206* (2013.01)

(58) Field of Classification Search
CPC .......... A61M 5/20; A61M 2005/14268; A61M 5/141; A61M 5/2448; A61M 5/284; A61M 5/31596; A61M 5/3294; A61M 3/005; A61M 5/16827; A61M 16/14; A61M 2039/0027; A61M 5/1409; A61M 2005/2451; A61M 5/2455; A61M 2205/0294; A61M 2202/06; A61M 2202/064
USPC ........................................ 604/67, 141, 191
See application file for complete search history.

(56) References Cited

U.S. PATENT DOCUMENTS

| | | | |
|---|---|---|---|
| 6,458,118 B1 * | 10/2002 | Lent | A61M 5/14276 604/288.01 |
| 2010/0318035 A1 * | 12/2010 | Edwards | A61M 5/19 604/187 |
| 2014/0005596 A1 * | 1/2014 | Schuster | A61M 5/5086 604/67 |
| 2014/0107579 A1 * | 4/2014 | Lanigan | G01F 13/00 604/151 |
| 2015/0105750 A1 * | 4/2015 | Laugharn, Jr. | A61L 2/0011 604/513 |

FOREIGN PATENT DOCUMENTS

| | | | | |
|---|---|---|---|---|
| WO | WO 8802265 A1 * | 4/1988 | .......... | A61M 5/2066 |
| WO | 2012/011909 A1 | 1/2012 | | |

OTHER PUBLICATIONS

International Preliminary Report on Patentability issued in PCT/US2015/056081 dated Apr. 18, 2017.

* cited by examiner

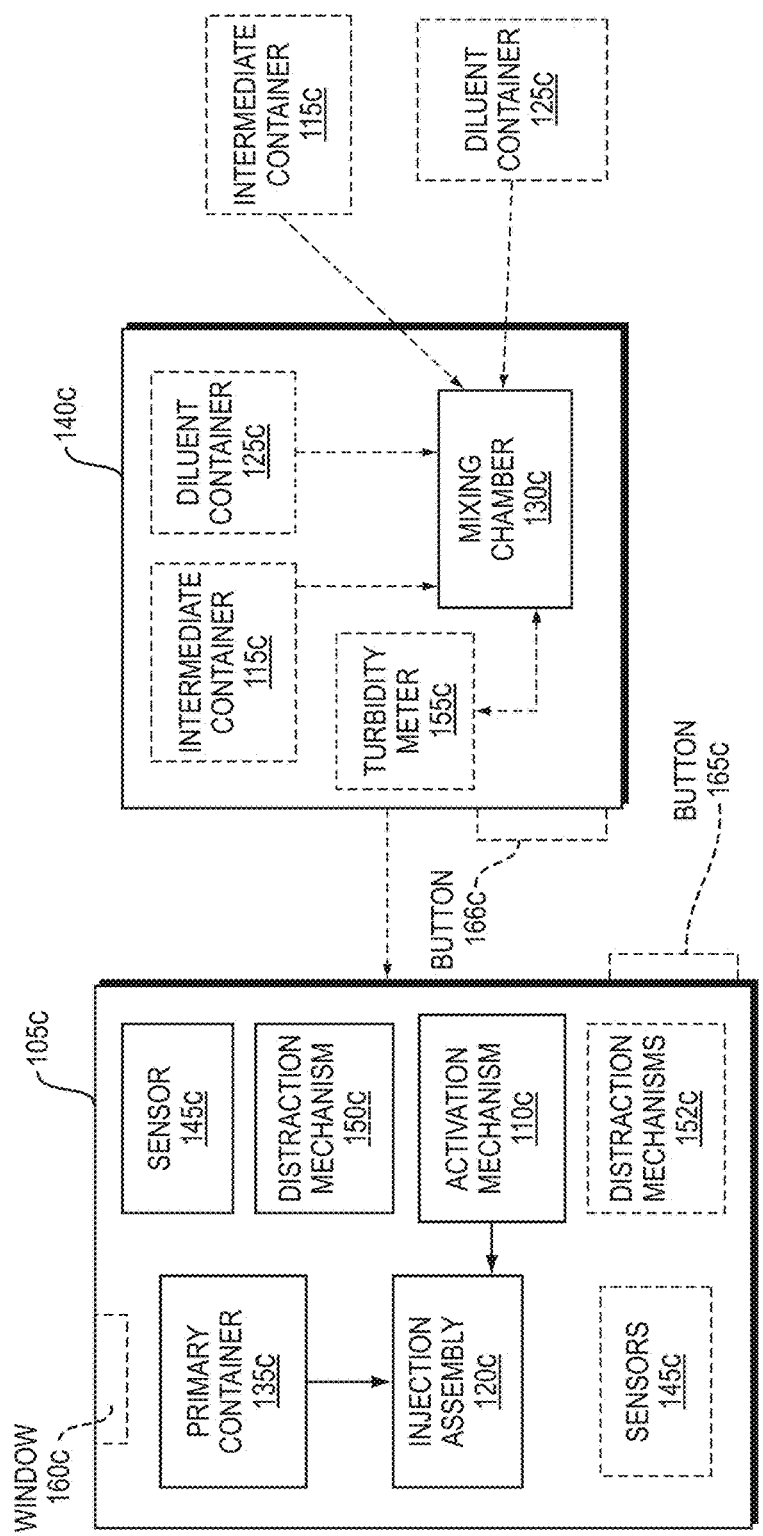

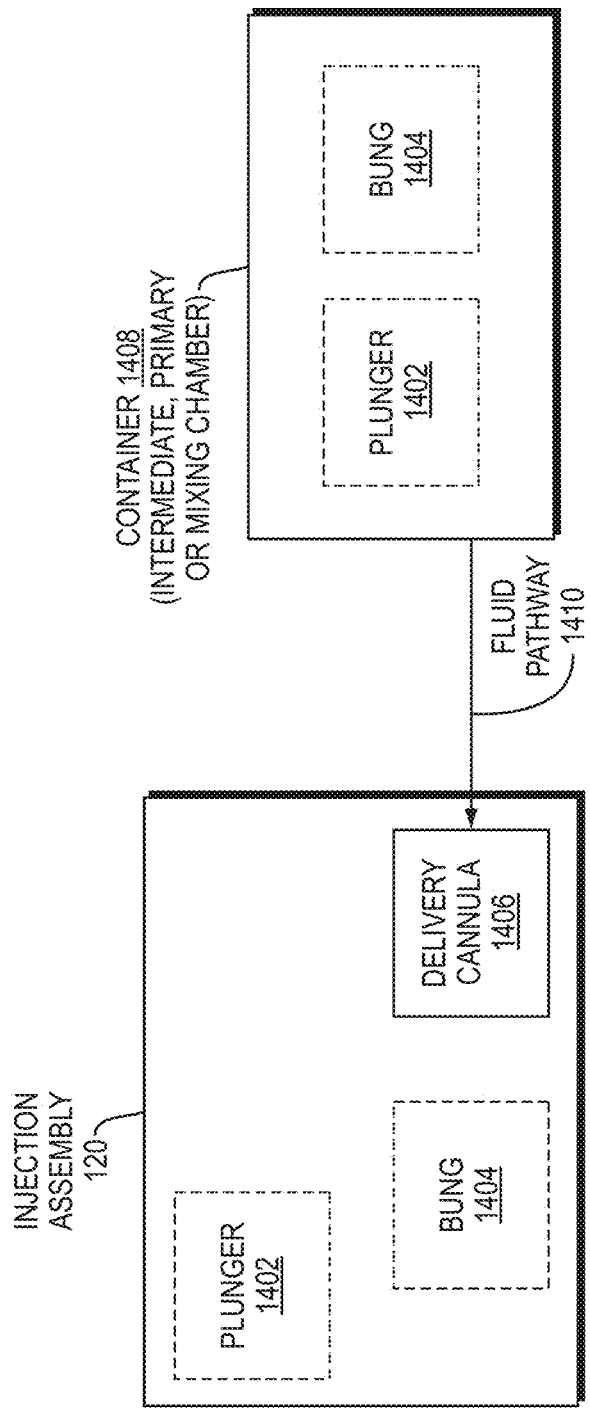

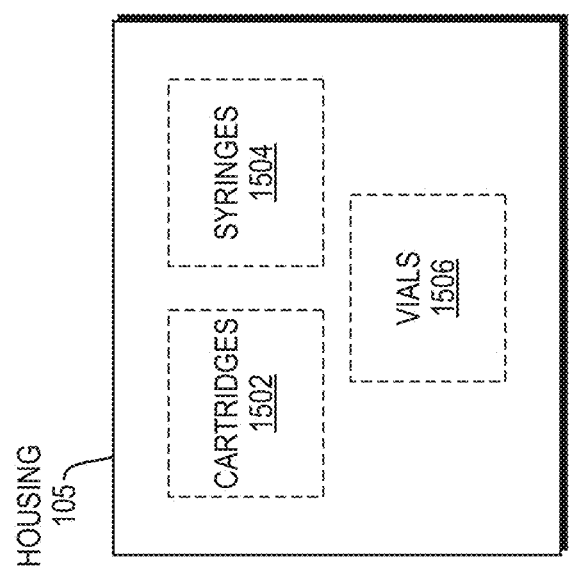

WEARABLE AUTOMATIC INJECTION SYSTEM AND APPARATUS

RELATED APPLICATIONS

This application is related to and claims the benefit of priority to U.S. Provisional Patent Application No. 62/065,647, filed Oct. 18, 2014, and is related to U.S. Provisional Patent Application No. 61/893,123, filed Oct. 18, 2013, and PCT Application No. PCT/US2014/061279, filed Oct. 18, 2014, the entire contents of each application are expressly incorporated herein in their entirety by reference.

BACKGROUND

Automatic injection devices offer an alternative to manually-operated syringes for administering medicaments into patients' bodies and allowing patients to self-administer medications. Conventionally, an automatic injection device houses a syringe and, when operated, causes the syringe to move forwardly and a needle to project from the housing so that a medicament contained in the syringe is administered to a patient's body. Conventional automatic injection devices include hand-held automatic injection devices and patch pumps, which are patient-mounted auto-injectors. In use, a patch pump containing a medicament is mounted onto the body or clothing of a patient and triggered to administer the medicament to the patient.

SUMMARY OF INVENTION

In one embodiment, a wearable automatic injection device for administering a final medicament to a patient is provided. The wearable automatic injection device comprises a housing including an intermediate container holding a bulk intermediate medicament, a mixing chamber including one or more mixing mechanisms to mix the bulk intermediate medicament and a diluent to form the final medicament. In some embodiments, the housing can include an activation mechanism for initiating an injection assembly after the final medicament is formed to administer the final medicament to the patient. The activation mechanism initiates the mixing mechanism based on a user actuating the wearable automatic injection device. The housing can include an injection assembly including a needle and a fluid pathway for injecting the patient with the final medicament. The intermediate container can hold or include the diluent. The intermediate container can store the bulk intermediate medicament and diluent separately. The housing can include a second container holding the diluent, and the mixing chamber is in fluid communication with the intermediate container and the second container.

The wearable automatic injection device can include a turbidity meter to automatically verify mixing of the bulk intermediate medicament and the diluent. The wearable automatic injection device can include an inspection window disposed in the housing for a user to visually inspect the final medicament.

The bulk intermediate medicament is in dry form. In some embodiments the bulk intermediate medicament is dried by lyophilization, spray freeze dried, or spray dried. In some embodiments, the bulk intermediate medicament is coated on an inner surface of the container.

The wearable automatic injection device can include a piezoelectric element coupled to the container and energized by the activation mechanism when the mixing mechanism is initiated. The piezoelectric element is configured to cause the diluent to cavitate or the bulk intermediate medicament to fracture and to release from the container surface into the diluent. The intermediate container can include a barrier having an orifice axially disposed in the container. The intermediate container can include a porous element having the bulk intermediate medicament within, disposed at a proximal end of the intermediate container. The intermediate container can include an impeller to cause oscillation of the diluent in the intermediate container. The mixing chamber can include an impeller to cause oscillation of the diluent in the mixing chamber.

In another embodiment, a system for administering a final medicament to a patient is provided. The system includes a first container holding a bulk intermediate medicament, a second container holding a diluent to be mixed with the bulk intermediate medicament to form the final medicament, a mixing mechanism including a mixing container for mixing the bulk intermediate medicament and the diluent in the mixing container to form the final medicament prior to injection, and a wearable automatic injection device. The wearable automatic injection device includes a housing, a port to receive the mixing container containing the final medicament, an injection assembly for injecting the patient with the final medicament, and an activation mechanism for initiating the injection assembly for administering the final medicament to the patient. The mixing mechanism is initiated based on a user actuating the mixing mechanism. The mixing mechanism can be initiated by a user actuating a wireless remote in wireless communication with the mixing mechanism.

In some embodiments, the system can include a turbidity meter disposed in the mixing mechanism to automatically verify mixing of the bulk intermediate medicament and the diluent. In some embodiments, the system can include an inspection window disposed in the housing for a user to visually inspect the final medicament.

In some embodiments, the mixing container stores the bulk intermediate medicament and diluent separately. The bulk intermediate medicament is in dried form. In some embodiments, the bulk intermediate medicament is a powder or plurality of solid units. The bulk intermediate medicament is dried by lyophilization, spray freeze dried, or spray dried. In some embodiments, the bulk intermediate medicament is in liquid form. In some embodiments, the bulk intermediate medicament is coated on an inner surface of the mixing container.

The system can include a piezoelectric element coupled to the mixing container and energized by the mixing mechanism when the mixing mechanism is initiated. The piezoelectric element is configured to cause the drug to release from the mixing container surface into the diluent. The mixing container can include a barrier having an orifice axially disposed in the mixing container. In some embodiments, the mixing container can include a porous element having the bulk intermediate medicament dried within, disposed at a proximal end of the mixing container. In some embodiments, the mixing container can include a valve separating the bulk intermediate medicament and the diluent. The valve configured to open to allow mixing of the bulk intermediate medicament and the diluent to form the final medicament. In some embodiments, the mixing container can include a micro-tube axially disposed therein. The micro-tube having a coating of the bulk intermediate medicament. In some embodiments, the mixing container can include a gas vent configured to allow gas to escape prior to the injection. The mixing mechanism is configured to cause agitation of the mixing container to thoroughly mix the bulk intermediate medicament and the diluent.

In another embodiment, a system for administering a final medicament to a patient is provided. The system includes a mixing mechanism for mixing a bulk intermediate medicament and a diluent to form the final medicament prior to injection, and a wearable automatic injection device. The wearable automatic injection device includes a housing, a primary container to hold the final medicament, an injection assembly for injecting the patient with the final medicament, and an activation mechanism for initiating the injection assembly for administering the final medicament to the patient. In some embodiments, the mixing mechanism is configured to store the bulk intermediate medicament and the diluent separately. The mixing mechanism can include a vortex generator having the bulk intermediate medicament coated on the inner surface. The vortex generator is configured to receive the diluent from an inlet and generate a vortex movement to mix the bulk intermediate medicament and diluent to form the final medicament.

In some embodiments, inert solid beads are entrained in the fluid vortex and their motion against the mixing container walls serves to mechanically disperse and grind the bulk intermediate medicament.

In some embodiments, the mixing mechanism includes a venturi system configured to mix the bulk intermediate medicament and the diluent using a reduction in fluid pressure in the system.

In another embodiment, a wearable automatic injection device for administering a final medicament to a patient is provided. The wearable automatic injection device includes a housing having a chamber for holding a bulk intermediate medicament and a diluent, and a mixing mechanism operatively coupled to the chamber for mixing a bulk intermediate medicament and a diluent. The chamber includes a first compartment for holding the bulk intermediate medicament and a second compartment for holding the diluent. The first compartment and the second compartment are initially sealed and separated from each other. The first compartment and the second compartment are in fluidic communication with each other.

In another embodiment, a wearable automatic injection device for administering a final medicament to a patient is provided. The wearable automatic injection device includes a housing having a chamber for holding a bulk intermediate medicament and a diluent, a fluid pathway extending between the chamber and a delivery cannula, and a mixing mechanism operatively coupled to the fluid pathway for mixing the bulk intermediate medicament and the diluent flowing through the fluid pathway. The chamber includes a first compartment for holding the bulk intermediate medicament and a second compartment for holding the diluent. The first compartment and the second compartment are initially sealed and separated from each other. The first compartment and the second compartment are in fluidic communication with each other.

In some embodiments, the wearable automatic injection device can include a vibration mechanism coupled to the housing. When the vibration mechanism is activated it causes the wearable automatic injection device to vibrate against the patient's skin, before, during or after an injection to distract the patient from pain caused by the injection. In some embodiments, the wearable automatic injection device can include a pressure sensor coupled to the housing to detect contact between the wearable injection device and the patient's skin.

In some embodiments, the wearable automatic injection device can include a cooling mechanism coupled to the housing. The cooling mechanism when activated, causes cooling of the wearable automatic injection device before, during or after an injection to distract the patient from perceived pain caused by the injection. In some embodiments, the wearable automatic injection device can include a pressure sensor coupled to the housing to detect contact between the wearable injection device and the patient's skin. In some embodiments, the wearable automatic injection device can include a temperature sensor coupled to the housing to detect a temperature of the wearable injection device.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 1C is a block diagram of the components of a wearable injection device and an activation mechanism, according to an example embodiment;

FIG. 14 illustrates an injection assembly for exemplary embodiments of the wearable injection device, according to an example embodiment; and FIG. 15 illustrates a wearable injection device including a plurality of cartridges, syringes, or vials, according to an example embodiment.

DETAILED DESCRIPTION

Figure 1A:
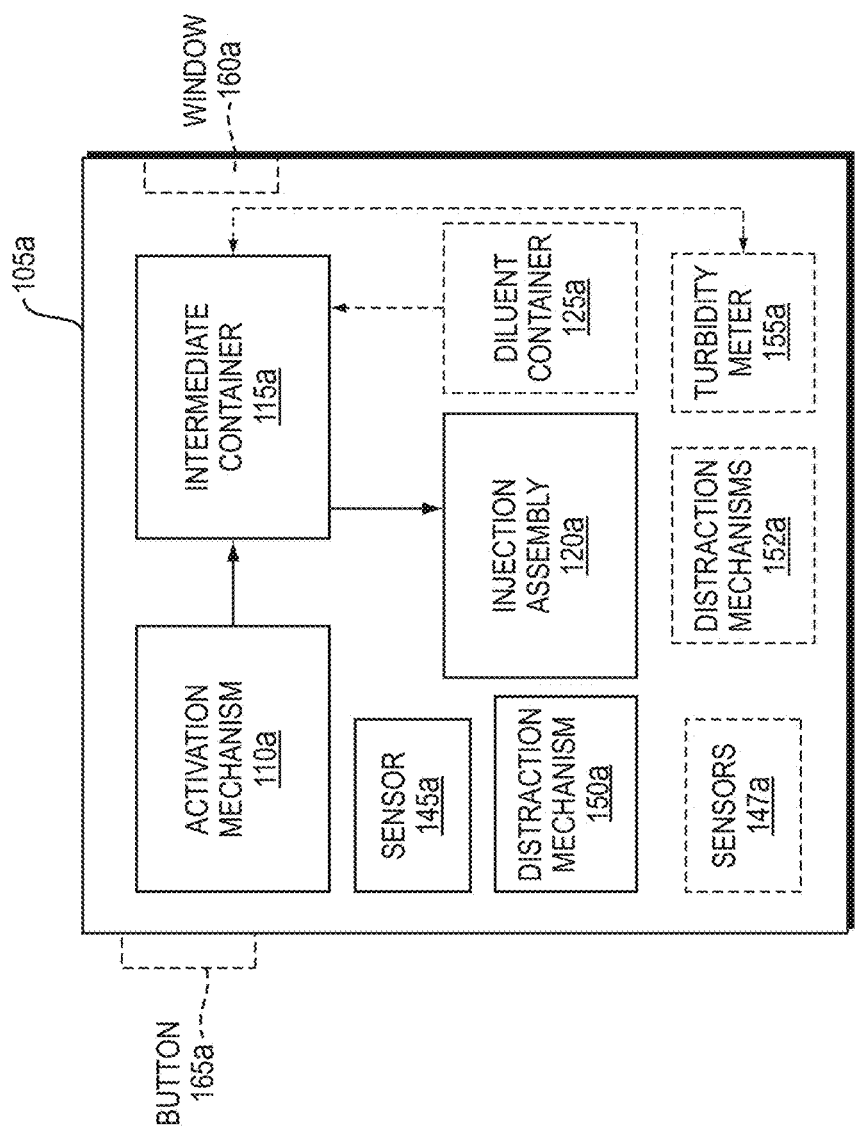
FIG. 1A is a block diagram of the components of a wearable injection device, according to an example embodiment.

Injection is a primary mode of medicament delivery and involves administering a bolus of a medicament into a patient. Injections are highly effective in administering various medicaments including insulin, vaccines, and drugs that may need to be reconstituted before delivery. Some medicaments are stored in dry form, for example, lyophilized, to increase product stability. These drugs have to be reconstituted or mixed with a liquid, called the diluent, before they can be administered.

As used herein, the term "patient" or "user" refers to any type of animal, human or non-human, that may receive an administration of a medicament using exemplary wearable injection devices.

As used herein, the terms "wearable automatic injection device," "wearable autoinjector," and "wearable injection device" refer to a device worn by a patient that enables the patient to self-administer an effective dose of one or more medicaments by either fastening the wearable device directly to his or her skin, manually positioning the wearable device to his or her skin during the time of self-administration, or fastening the wearable device to an article of clothing that allows the device to interface with the patient's body. In some examples described herein, the wearable device may differ from a conventional syringe by the inclusion of a mechanism or mechanisms for mixing or reconstituting a bulk intermediate medicament in dry or liquid form prior to injections and by delivering volumes that are considered too large for a subcutaneous bolus delivery (typically >1.2 mL). In some embodiments, the mixing mechanisms mixes one or more dried medicaments and one or more diluents, or one or more liquid medicaments with one or more diluents, or one or more dried medicaments and one or more liquid medicaments with a mechanical mechanism, an electromechanical mechanism, an electrochemical mechanism, or any combination thereof. In some embodiments, the wearable injection device includes a delivery cannula comprising an injection needle, a trocar, a cannula, a catheter, or a combination thereof, to deliver a medicament to a patient.

As used herein, the term "medicament" refers to a composition intended for use in medical diagnosis, cure, treatment, or prevention of disease. A medicament may be a therapeutic agent or a combination of therapeutic agents. A medicament may include a therapeutic protein, for example, a peptide or antibody, or antigen-binding portion thereof. A medicament may include an anesthetic, for example, novocaine, procaine, lidocaine, prilocaine, and the like. In one embodiment, a medicament is a "bulk intermediate medicament." In another embodiment, a medicament is a "final medicament." In yet another embodiment, a medicament represents a mixture of two or even more pharmacologically active agents.

As used herein, the term "bulk intermediate medicament" refers to a liquid medicament, dried medicament (powder, solid units, lyophilized, spray freeze dried, spray dried, and the like), or solid medicament (or plurality thereof or combination thereof) that includes a medicament that is represented for use in a final medicament and that, when used in the manufacturing, processing, or packaging of the medicament, becomes a final medicament. A dried or solid bulk intermediate medicament may be provided in the amount of 0.1 μg to 1 gram or more. A liquid bulk intermediate medicament may be provided in the amount of 0.10 μL to 5 mL or more.

As used herein, the term "final medicament," refers to a composition in a form suitable for administration to a user or patient, e.g., a human subject, for medical purposes. In one embodiment, a final medicament includes a bulk intermediate medicament (in liquid form, in dried form (powder, solid units, lyophilized, spray freeze dried, spray dried, and the like), solid form, or a combination thereof) and a diluent. In one embodiment, a final medicament includes a plurality of solid units including a therapeutic protein/antibody combined with water resulting in a final medicament which may be administered to a human subject. In another embodiment, a final medicament includes an intermediate medicament and a solution of a pharmacologically active agent serving as a diluent, e.g., a plurality of solid units including a therapeutic protein/antibody combined with a solution of a pharmacologically active agent results in a final medicament which may be administered to a human subject. In one embodiment, a final medicament is a reconstituted formulation comprising solid units in a diluent, e.g., water. In another embodiment, a final medicament is a solid unit including for example a therapeutic protein and a polymer, e.g., an enteric coating. In another embodiment, the final medicament is a combination of a bulk intermediate medicament in liquid form and a diluent in liquid form. In another embodiment, the final medicament is a combination of two or more bulk intermediate medicaments in liquid form, in dried form (powder, solid units, lyophilized, spray freeze dried, spray dried, and the like), solid form, or a combination thereof. The final medicament may be in the amount of 0.10 μL to 5 mL or more.

As used herein, the term "diluent" refers to a liquid to mix with a bulk intermediate medicament to form a final medicament that is administered to a human subject. In one embodiment, the diluent may be water. In another embodiment, the diluent may be a second bulk intermediate medicament to be mixed with a first bulk intermediate medicament. The diluent may be provided in the amount of 0.10 μL to 5 mL or more.

The term a "primary container," as used herein, refers to an article of manufacture which contains or is intended to contain a final medicament suitable for the intended use of the final medicament. In some embodiments, the primary container is a syringe, a cartridge, a vial, or any combination thereof. In some embodiments, the primary container may be multiple containers. In one embodiment, the primary container is a dual chamber syringe which contains a bulk intermediate medicament in liquid form, in dried form (powder, solid units, lyophilized, spray freeze dried, spray dried, and the like), solid form, or a combination thereof. In one embodiment, the primary container is a dual chamber syringe which contains a plurality of solid units including for example a therapeutic protein and water.

The term an "intermediate container," as used herein, refers to an article which holds or is intended to contain a bulk intermediate medicament prior to further processing to become a final medicament of the active ingredient, for example, a therapeutic protein. In some embodiments, the intermediate container is a syringe, a cartridge, a vial, a tubing, a porous inert solid matrix, or any combination thereof. In some embodiments, the intermediate container may be multiple containers. Some embodiments may include a primary container and an intermediate container, or a primary container, or an intermediate container.

The term a "syringe," as used herein, refers to a container, including a moveable bung, for holding a medicament. In one embodiment, a syringe includes a plunger, and a needle. In another embodiment, a syringe may be attachable to a needle and a plunger. A syringe may be a primary container or an intermediate container as discussed below.

The term a "cartridge" as used herein, refers to a container, including a septum and a bung, for holding a medicament. In one embodiment, a cartridge may be attachable to a needle and a plunger. A cartridge may be a primary container or an intermediate container as discussed below.

The terms a "vial" as used herein, refers to a container for holding a medicament with a rubber stopper covering an end of the container and a metal cap crimped on the rubber stopper. In one embodiment, a vial includes a flip-top or a snap-cap that a user can flip off prior to use of the vial. In another embodiment, a vial includes a cork stopper or a plastic stopper.

As used herein, the term "mixture" refers to a mixture of the bulk intermediate medicament and the diluent to form a final medicament to be administered to a patient. In one embodiment, the mixture may be a slurry that is a semiliquid mixture of the diluent and the bulk intermediate medicament. In one embodiment, the mixture may be a suspension that is a heterogeneous mixture containing solid particles of the bulk intermediate medicament in the diluent that may be sufficiently large for sedimentation. In another embodiment, the mixture represents a solution that is a homogenous mixture where all of the bulk intermediate medicament particles are fully or partially dissolved in the diluent.

As used herein, the term "mixing" refers to combining the bulk intermediate medicament and the diluent to produce a mixture. In one embodiment, mixing refers to reconstituting of the bulk intermediate medicament using the diluent to produce a mixture, such as a reconstituted solution. In one embodiment, mixing includes agitation of a bulk intermediate medicament and a diluent to cause mixing. In another embodiment, mixing includes agitation of the mixture, formed by mixing a bulk intermediate medicament and a diluent, to ensure complete mixing, for example, reconstitution of the bulk intermediate medicament and the diluent.

Exemplary embodiments provide wearable automatic injection devices that may adhere to the skin or clothing of the patient and deliver a reconstituted medicament into the patient by injection. The wearable automatic injection device may be clipped to a belt of a user. The medicament may be delivered to the patient via a fluid conduit or tube through a butterfly needle inserted in the patient skin. The injection may be any type of injection including, but not limited to, subcutaneous injection, intramuscular injection, intravenous injection, intradermal injection, transdermal injection, microarray needles injection, and the like. Exemplary wearable injection devices also include mechanisms for reconstituting or mixing medicaments prior to administration. Exemplary wearable injection devices may be reusable or disposable. Exemplary wearable injection devices may be battery operated or battery-less.

Exemplary embodiments are described below with reference to certain illustrative embodiments. While exemplary embodiments are described with respect to using a wearable automatic injection device to provide an injection of a dose of a final medicament, one of ordinary skill in the art will recognize that exemplary embodiments are not limited to the illustrative embodiments and that exemplary wearable automatic injection devices may be used to mix a diluent and a bulk intermediate medicament, and in turn, enable delivery of the mixture into a patient. In addition, components of exemplary automatic injection devices are not limited to the illustrative embodiments described below.

In exemplary embodiments of mixing mechanisms or chambers, a user may initiate the mixing process by actuating a button (disposed on the wearable injection device or the mixing system) or by toggling or sliding a lever (on the wearable injection device or the mixing system). Some embodiments may include a touch-screen interface for receiving input from a user to initiate the mixing process and the injection process or to manage the wearable injection device and a mixing unit. Some embodiments may include a speech recognition module that can receive verbal commands from a user to initiate the mixing process and the injection process, and to manage the wearable injection device and a mixing unit. This user action may trigger the activation mechanism, which in turn may initiate the mixing process by allowing the diluent and bulk intermediate medicament to mix, and in some embodiments by causing agitation of the diluent and bulk intermediate medicament. Agitation may be performed by rocking the container, by vigorously shaking the container, by using high frequency sonic waves, by rotating the container, by inducing turbulent, high shear fluid flow, and/or by any other suitable means, including those that increase the surface are between a medicament and a diluent during dissolution and mixing process immediately before or during the injection process.

In some embodiments, agitation is performed by the wearable injection device to complete mixing, including, but not limited to, combining diluent and medicament rotating along the longitudinal or latitudinal axis or other suitable means. In other embodiments, a mixing unit may be provided separately from the wearable injection device. The mixing unit may be provided to the user as an accessory to the wearable injection device in the form of a docking station or a hub system that is capable of receiving one or more containers (intermediate container and mixing container) and a mixing activation mechanism (that initiates the mixing process). The user may be able to couple or install various components on the docking station or hub system to initiate and complete mixing of the bulk intermediate medicament and the diluent. In some embodiments, the wearable injection device (with the intermediate container or mixing container) can be installed on the mixing unit for agitation.

In an example embodiment, the mixing unit may cause the combination of a diluent and a bulk intermediate medicament to initiate the mixing process, and then performing agitation, if needed, to ensure complete mixing of the diluent and the bulk intermediate medicament. In another example embodiment, the wearable injection device may cause the combination of a diluent and a bulk intermediate medicament, and the mixing unit performs agitation, if needed, to ensure complete mixing. In yet another example embodiment, a user may cause the combination of a diluent and a bulk intermediate medicament to initiate the mixing process, then install the wearable injection device or the containers on the mixing unit for agitation.

Alternatively, the user may manually mix the bulk intermediate medicament by transferring a diluent to an intermediate container holding the bulk intermediate medicament, and agitating the container to mix and form the final medicament. The user can manually perform agitation, for example in emergency situations, if he does not have immediate access to the mixing unit.

Exemplary embodiments of the wearable injection device includes components for inspecting the medicament. For example, the housing of the injection device may include an inspection window through which a user can view the contents (medicament) of the injection device. The user can visually inspect the medicament to determine whether mixing has occurred prior to performing the injection. In some embodiments, the color of the final medicament may be different from the color of the bulk intermediate medicament and the diluent, so that a user visually determines the difference between the final medicament and the diluent. In some embodiments, the final medicament may be cloudy while the diluent is clear, aiding in the user's visual inspection.

In some embodiments, the wearable injection device may include an automated inspection means. For example, the device may include a turbidity meter that measures the cloudiness or haziness of the final medicament. The turbidity meter may determine whether mixing is complete based on a configurable threshold measurement. The threshold measurement may be configured by the manufacturer prior to distribution or sale based on the mixing requirements of the medicament being injected by the wearable injection device. In an example embodiment, the turbidity meter may automatically trigger the injection process, for example via the activation mechanism, when the threshold measurement of the cloudiness of the final medicament is satisfied.

Exemplary embodiments of the wearable injection devices may be capable of administering a final medicament at various rates. For example, in an example embodiment, the wearable injection device may administer the final medicament by ejecting it through the injection needle at a fixed injection rate over a period of time. In another example embodiment, a user may be able to select injection rate or injection time that the wearable injection device may administer the final medicament. For example, the user may select between slow, medium or fast injection rate, either by selecting the option or by specifying the period of time over which the injection should be administered. In another embodiment, the wearable injection device may be capable of administering the final medicament over a variable injection profile configured by the user or the manufacturer. For example, the injection may start at a slow injection rate, then speed up either until injection is completed, or then speed up towards the middle of the injection process, and slow down at the end of the injection process. Exemplary embodiments of the wearable injection device are capable of administering an injection over a duration of 2 seconds to 2 hours or as long as 72 hours. The injection profile may factor in a patient's age, weight, gender, disease, treatment protocol, medicament, and other factors. In some embodiments, during the injection process small amounts of air is delivered to patient along with the final medicament. For example, about 100-200 microliters of air may be injected into the patient body during delivery, along with the final medicament.

Exemplary embodiments provide wearable injection devices that adhere to the user or patient's body. Exemplary wearable injection devices are capable of adhering and administering an injection at various sites on the patient including, but not limited to, abdomen, upper thigh, arm, and the like. The wearable injection device may adhere to the skin via an adhesive layer included on a surface of the housing. Alternatively, the wearable injection device may be secured to the skin using a strap, belt or other suitable mechanical means that is coupled to the housing of the injection device. In another example embodiment, the wearable injection device may be secured to the skin via a suction mechanism with or without using a gel or liquid to aid in suction. In yet another example embodiment, the wearable injection device may be secured to the skin manually by the user until injection is completed.

In example embodiments, the wearable injection device includes a catheter to administer the injection to a patient. The catheter may be part of an implantable subcutaneous or intramuscular access system. The catheter may be manually or automatically removed from the skin, and may be automatically retracted into the housing after the injection process is complete.

Exemplary embodiments of the wearable injection device provide for automatic retraction of the injection needle after the injection device is removed from the skin either after completion of the injection process or during the injection process in the event that the device loses contact with the skin. This mechanism protects from accidental needlesticks. In some embodiments, the wearable injection device includes a needle sleeve extending from the wearable injection device to shield the patient and others from needlesticks.

Some embodiments of the wearable injection device include various indications to the user at different stages of the reconstitution and injection process. For example, the indications such as visual, audible, and/or tactile indications may be provided by the wearable injection device to indicate different stages and/or states of the injection device. The indications may be provided via wireless transmissions. In some embodiments, the indications may indicate the start of the injection process where the injection needle is ready to eject the final medicament, the completion of the injection process where a dose of the medicament has been delivered, the start of the mixing process where the bulk intermediate medicament begins mixing with the diluent, the end of the mixing process where the mixing of the final medicament is complete.

Some embodiments of the wearable injection device include a skin-sensor coupled to an outer surface of the housing. The skin-sensor may automatically trigger retraction of the injection needle when it is determined that the wearable injection device is no longer in contact with the patient's skin. Additionally, the skin-sensor may automatically trigger advancement of the injection needle when at the start of the injection process it is determined that the wearable injection device is in contact with the patient's skin as required by the injection device. In some embodiments, the skin-sensor automatically triggers the actuation mechanism to initiate ejection of the final medicament when appropriate. In other words, the skin-sensor can prevent the wearable injection device from ejecting the final medicament before the injection device is in contact with the skin and/or before the injection needle is inserted into the patient. The skin-sensor may be a sensor that detects skin or it may be a surface sensor that detects resistance by a surface or it may be a mechanical interlock or switch actuated by physical contact.

Some embodiments of the wearable injection device includes vibratory mechanisms that vibrate the device or cooling mechanisms that cool a surface of the device or a combination thereof. Vibrating the wearable injection device and/or cooling the device before or during the injection process may distract the patient from the injection process when the wearable injection device is placed on the patient's skin. For example, the wearable injection device may include temperature sensors or pressure sensors or a combination thereof that provide feedback to the vibratory mechanisms or the cooling mechanisms. Thus, when the wearable injection device is engaged with the patient's skin results in a perceived low-pain or no-pain sensation during delivery of the medicament due to the vibration of the device, cooling of a surface of the device or both. The wearable injection device also may include any other mechanisms to confuse or distract the senses of a user, for example, audio source emitting an audible sound, or sound pulses felt by the user.

In some embodiments, the wearable injection device also may include an audible or visual indicator to indicate completion of an injection, or end of delivery of a dose of the final medicament, or that the injection device is substantially empty of the final medicament.

In example embodiments, the primary package includes a wearable automatic injection device, a container holding a medicament, and/or a radio-frequency identification (RFID) tag. The RFID tag may identify the medicament provided in the primary packaging. The RFID tag may also track the location of the package and verify whether the correct medicament was delivered to the correct patient or medical institution. Similarly, other means for identification and tracking can also be included in the primary package, for example, the components in the primary package and the primary package itself may include a barcode, a 2D bar code, a QR code, and the like. In some embodiments, the primary package may be coupled or electronically linked to a computer or mobile phone application (i.e. app) for identifying and tracking the primary package for example via near field communication (NFC), or Bluetooth.

In further example embodiments, the wearable injection device, the primary package or both may include the capability of data communications via an Internet or Bluetooth connection. The injection device may be capable of gathering data related to the injection process and communicating the data toward a database.

In some embodiments the activation mechanism, as described herein, operates to initiate the injection process via the injection assembly. In other embodiments, the activation mechanism operates to initiate the mixing process via various mixing mechanisms and mixing chambers described herein. In yet other embodiments, the activation mechanism operates to initiate the injection process and the mixing process. The activation mechanism may be activated using a button provided in exemplary embodiments.

FIG. 1A is a block diagram of an exemplary wearable injection device. The wearable injection device includes a housing 105a. In some embodiments, the housing 105a includes an activation mechanism 110a, an intermediate container 115a holding a bulk intermediate medicament, an injection assembly 120a, a sensor 145a, sensors 147a, a distraction mechanism 150a, distraction mechanisms 152a, a turbidity meter 155a, a window 160a, and a button 165a. In some embodiments, the housing 105a also may include a diluent container 125a holding a diluent. In some embodiments, portions of the activation mechanism 110a may be outside of the housing. The button 165a may be associated with the activation mechanism 110a, where actuation of the button 165a causes the activation mechanism 110a to operate. In an example embodiment, the intermediate container 115a may contain the bulk intermediate medicament and the diluent stored separately until it is time for mixing. In some embodiments, the intermediate container 115a may include a mixing mechanism, such that when the diluent is introduced to the intermediate container 115a the mixing mechanism performs mixing of the bulk intermediate medicament and the diluent to produce a mixture (the final medicament). Various examples of mixing mechanisms are discussed in detail below. The injection assembly 120a may include a delivery cannula comprising an injection needle, a trocar, a cannula, a catheter, or a combination thereof, for delivering the final medicament to the patient. The injection assembly 120a may be fluidically coupled to the intermediate container 115a and the activation mechanism 110a for injection of the mixture into a patient via the injection needle.

In some embodiments, the housing 105a may include multiple sensors 147a. The sensor 145a may be a temperature sensor or a pressure sensor or a combination thereof to sense a temperature of the housing 105a or to sense engagement with patient skin. In some embodiments, the sensor 145a also may include a sensor to sense when the injection device is substantially empty of the final medicament or when a dose of the final medicament has been ejected. In some embodiments, the housing 105a may include multiple distraction mechanisms 152a. The distraction mechanism 150a may be a mechanism to cause vibration of the housing 105a or a mechanism to cause cooling of the housing 105a, so that the patient is distracted from the pain of the injection needle. The distraction mechanism 150a also may include a mechanism to generate an audible sound to distract the patient from the pain of the injection. The distraction mechanism 150a also may include a mechanism to generate sound pulses that can be felt by the patient to distract him or her from the pain of the injection. The distraction mechanism 150a also may include a mechanism to cause a temperature differential. In some embodiments, the sensor 145a or the distraction mechanism 150a may be provided outside of the housing 105a.

In some embodiments, the housing 105a includes the window 160a for inspection through which a user can view the contents of the wearable injection device. The user can visually inspect the final medicament in the intermediate container 115a to determine whether mixing has occurred prior to performing the injection. In some embodiments, the color of the final medicament may be different from the color of the bulk intermediate medicament and the diluent, so that a user visually determines the difference between the final medicament and the diluent. In some embodiments, the final medicament may be cloudy while the diluent is clear, aiding in the user's visual inspection. In some embodiments, the window 160a is located on the housing 105a such that the user can view the other components of the wearable injection device.

In some embodiments, the wearable injection device includes the turbidity meter 155a for an automated inspection means. The turbidity meter 155a may be coupled to the intermediate container 115a, and measures the cloudiness or haziness of the final medicament in the intermediate container 115a. The turbidity meter may determine whether mixing is complete based on a configurable threshold measurement. The threshold measurement may be configured by the manufacturer prior to distribution or sale based on the mixing requirements of the medicament being injected by the wearable injection device. In an example embodiment, the turbidity meter may automatically initiate the injection process, for example via the activation mechanism 110a, when the threshold measurement of the cloudiness of the final medicament is satisfied.

Figure 1B:
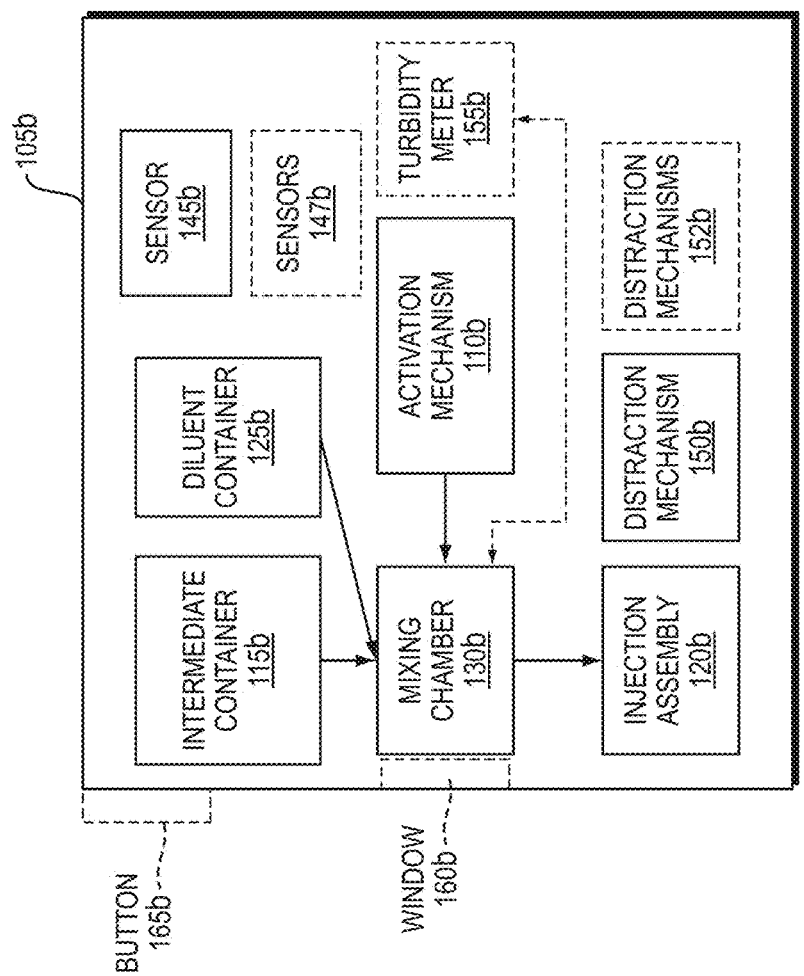
FIG. 1B is a block diagram of the components of a wearable injection device, according to an example embodiment.

FIG. 1B is a block diagram of another exemplary wearable injection device. In this embodiment, the wearable injection device housing 105b includes an activation mechanism 110b, an intermediate container 115b for holding a bulk intermediate medicament, an injection assembly 120b, a diluent container 125b for holding a diluent, a mixing chamber 130b, a sensor 145b, sensors 147b, a distraction mechanism 150b, distraction mechanisms 152b, a turbidity meter 155b, a window 160b, and a button 160b. The activation mechanism 110b may initiate the mixing process, at which point the bulk intermediate medicament from the intermediate container 115b and the diluent from the diluent container 125b are introduced to the mixing chamber 130b. The button 165b may be associated with the activation mechanism 110b, where actuation of the button 165b causes the activation mechanism 110b to operate. The mixing chamber 130b can include a mixing mechanism for mixing the bulk intermediate medicament and the diluent to produce a mixture that can be injected as the final medicament. Various examples of mixing mechanisms are discussed in detail below. The injection assembly 120b may include a delivery cannula comprising an injection needle, a trocar, a cannula, a catheter, or a combination thereof, for delivering the final medicament to a patient. The injection assembly 120b may be fluidically coupled to the mixing chamber 130b and the activation mechanism 110b for ejection of the mixture into a patient via the injection needle. The mixing chamber may also be referred to as the primary container as used herein.

In some embodiments, the housing 105 b may include multiple sensors 147b. The sensor 145 b may be a temperature sensor or a pressure sensor or a combination thereof to sense a temperature of the housing 105 b or to sense engagement with patient skin. In some embodiments, the sensor 145 a also may include a sensor to sense when the injection device is substantially empty of the final medicament or when a dose of the final medicament has been ejected. In some embodiments, the housing 105 b may include multiple distraction mechanisms 152 b. The distraction mechanism 150 b may be a mechanism to cause vibration of the housing 105 b or a mechanism to cause cooling of the housing 105 b, so that the patient is distracted from the pain of the injection needle. The distraction mechanism 150 b also may include a mechanism to generate an audible sound to distract the patient from the pain of the injection. The distraction mechanism 150 b also may include a mechanism to generate sound pulses that can be felt by the patient to distract him or her from the pain of the injection. The distraction mechanism 150 b also may include a mechanism to cause a temperature differential. In some embodiments, the sensor 145 b or the distraction mechanism 150 b may be provided outside of the housing 105 b.

In some embodiments, the housing 105b includes the window 160b for inspection through which a user can view the contents of the wearable injection device. The user can visually inspect the final medicament in the mixing chamber 130b to determine whether mixing has occurred prior to performing the injection. In some embodiments, the color of the final medicament may be different from the color of the bulk intermediate medicament and the diluent, so that a user visually determines the difference between the final medicament and the diluent. In some embodiments, the final medicament may be cloudy while the diluent is clear, aiding in the user's visual inspection. In some embodiments, the window 160b is located on the housing 105b such that the user can view the other components of the wearable injection device.

In some embodiments, the wearable injection device includes the turbidity meter 155b for an automated inspection means. The turbidity meter 155b may be coupled to the mixing chamber 130b, and measures the cloudiness or haziness of the final medicament in the mixing chamber 130b. The turbidity meter may determine whether mixing is complete based on a configurable threshold measurement. The threshold measurement may be configured by the manufacturer prior to distribution or sale based on the mixing requirements of the medicament being injected by the wearable injection device. In an example embodiment, the turbidity meter may automatically initiate the injection process, for example via the activation mechanism 110a, when the threshold measurement of the cloudiness of the final medicament is satisfied.

FIG. 1C is a block diagram of another exemplary wearable injection device where the mixing mechanism is located outside of the wearable injection device. In this embodiment, the wearable injection device housing 105c includes a primary container 135c for holding a final medicament, an activation mechanism 110c, an injection assembly 120c for injecting the final medicament into a patient, a sensor 145c, sensors 147c, a distraction mechanism 150c, distraction mechanisms 152c, and a button 165c associated with the activation mechanism 110c. The injection assembly 120c may include a delivery cannula comprising an injection needle, a trocar, a cannula, a catheter, or a combination thereof, for delivering the final medicament to a patient. A separate mixing mechanism 140c is provided outside of the housing 105c. The mixing mechanism 140c includes a mixing chamber 130c for mixing the bulk intermediate medicament and the diluent to produce a mixture to be injected into a patient. In some embodiments, the mixing mechanism 140c may include an intermediate container 115c for holding a bulk intermediate medicament and a diluent container 125c for holding a diluent. In some embodiments, the intermediate container 115c may be provided separately from the mixing mechanism 140c. In some embodiments, the diluent container 115 may be provided separately from the mixing mechanism 140c. The mixing mechanism 140c also may include a button 166c, where actuation of the button 116c may initiate the mixing process in the mixing mechanism 140c.

The mixing mechanism 140c allows the bulk intermediate medicament and the diluent to be mixed outside of the wearable injection device. Once mixed the container can be removed from the mixing mechanism 140c and loaded into the housing 105c of the wearable injection device to inject the final medicament into a user.

In some embodiments, the housing 105 c may include multiple sensors. The sensor 145 c may be a temperature sensor or a pressure sensor or a combination thereof to sense a temperature of the housing 105 c or to sense engagement with patient skin. In some embodiments, the sensor 145 c also may include a sensor to sense when the injection device is substantially empty of the final medicament or when a dose of the final medicament has been ejected. In some embodiments, the housing 105 c may include multiple distraction mechanisms. The distraction mechanism 150 c may be a mechanism to cause vibration of the housing 105 c or a mechanism to cause cooling of the housing 105 c, so that the patient is distracted from the pain of the injection needle. The distraction mechanism 150 c also may include a mechanism to generate an audible sound to distract the patient from the pain of the injection. The distraction mechanism 150 c also may include a mechanism to generate sound pulses that can be felt by the patient to distract him or her from the pain of the injection. The distraction mechanism 150 c also may include a mechanism to cause a temperature differential. In some embodiments, the sensor 145 c or the distraction mechanism 150 c may be provided outside of the housing 105 c.

In some embodiments, the housing 105c includes the window 160c for inspection through which a user can view the contents of the wearable injection device. The user can visually inspect the final medicament in the primary container 135c to determine whether mixing has occurred prior to performing the injection. In some embodiments, the color of the final medicament may be different from the color of the bulk intermediate medicament and the diluent, so that a user visually determines the difference between the final medicament and the diluent. In some embodiments, the final medicament may be cloudy while the diluent is clear, aiding in the user's visual inspection. In some embodiments, the window 160c is located on the housing 105c such that the user can view the other components of the wearable injection device.

In some embodiments, the mixing mechanism 140c includes a turbidity meter 155c for an automated inspection means. The turbidity meter 155c may be coupled to the mixing chamber 130c, and measures the cloudiness or haziness of the final medicament in the mixing chamber 130c. The turbidity meter may determine whether mixing is complete based on a configurable threshold measurement. The threshold measurement may be configured by the manufacturer prior to distribution or sale based on the mixing requirements of the medicament being injected by the wearable injection device.

The mixing mechanism 140c may initiate the mixing process, at which point the bulk intermediate medicament from the intermediate container 115c and the diluent from the diluent container 125c are introduced to the mixing chamber 130c. Once the mixture is formed, the mixture is introduced to the primary container 135c in the wearable injection device housing 105c. The primary container 135c and the injection assembly 120c may be fluidically coupled for ejection of the mixture during the injection process.

In exemplary embodiments shown in FIGS. 1A and 1B, the activation mechanism 110a and 110b may operate to initiate mixing of the bulk intermediate medicament and the diluent within the injection device. In these embodiments, the activation mechanism 110a, 110b also may operate to initiate the injection process, which may include movement or advancement of the injection needle outside of the housing 105a, 105b, dispensing of the contents of the wearable injection device, injection of mixture through the injection needle, or retraction of the injection needle into the housing 105a, 105b.

In the exemplary embodiment shown in FIG. 1C, where the separate mixing mechanism 140c is provided outside of the housing 105c, the activation mechanism 110c operates to initiate the injection process, which may include movement or advancement of the injection needle outside of the housing, injection of mixture through the injection needle, or retraction of the injection needle into the housing.

Although FIGS. 1A, 1B, and 1C illustrate the housing 105a, 105b, 105c, the activation mechanism 110a, 110b, 110c, the intermediate container 115a, 115b, 115c, the injection assembly 120a, 120c, 120b, the diluent container 125a, 125b, 125c, the mixing chamber 130b, 130c, the primary container 135c, mixing mechanism 140c, the sensor 145a, 145b, 145c, the sensors 147a, 147b, 147c, the distraction mechanism 150a, 150b, 150c, and the distraction mechanisms 152a, 152b, 152c in rectangular shapes, it should be understood that the components (housing, activation mechanism, intermediate container, injection assembly) of the wearable injection device may be of any shape or size, for example, cylindrical, spherical, rhomboid, polyhedral, constrained or unconstrained bladder, any combination thereof, or any other shape. Additionally, even though FIGS. 1A, 1B, and 1C illustrate the wearable injection device including the housing 105a, 105b, 105c, the activation mechanism 110a, 110b, 110c, the intermediate container 115a, 115b, 115c, the injection assembly 120a, 120c, 120b, the diluent container 125a, 125b, 125c, the mixing chamber 130b, 130c, the primary container 135c, mixing mechanism 140c, the sensor 145a, 145b, 145c, the sensors 147a, 147b, 147c, the distraction mechanism 150a, 150b, 150c, and the distraction mechanisms 152a, 152b, 152c, it should be understood that the exemplary wearable injection devices may include more or fewer components than illustrated.

In an example embodiment, the activation mechanism 110a, 110b, 110c is a mechanical mechanism based on mechanical principles, and operates without the use of a battery or electrical power. The mechanical activation mechanism may include a spring based mechanism. In an exemplary embodiment, the activation mechanism 110a, 110b, 110c may include one or more springs (e.g., a torsion spring, a leaf spring, a helical compression spring). The activation mechanism 110a, 110b, 110c may be in a retracted state before administration of a mixture and may be released during administration to actuate a bung or a plunger forwardly within a barrel portion of a container holding the final medicament (the intermediate container 115a, the mixing chamber 130b, or the primary container 135c) disposed in the housing 105a, 105b, 105c of the injection device. The wearable injection device can include a mechanical based activation mechanism operable by a user to start the mixing and the injection process, for example, a switch, a button, a lever, or the like.

In some embodiments, the user may use a touch-screen interface to operate the activation mechanism. The activation mechanism 110a, 110b, 110c can include a wireless based activation mechanism operable by the user to start the injection process, for example, an RFID proximity switch, a Wi-Fi proximity switch (actuated when it is near or in a Wi-Fi field), a proximity switch controlled via Wi-Fi, or other wireless receivers and switches to wirelessly receive a signal to start the injection process. The mixing and injection process may automatically introduce the diluent to the bulk intermediate medicament in the intermediate container 115a, or the mixing chamber 130b, 130c, mix the diluent and the bulk intermediate medicament to form a mixture, inject the mixture into the patient and withdraw the needle from the patient.

A wearable injection device with a mechanical activation mechanism may be a disposable injection device (one-time use device). The disposable wearable injection device may be preloaded with the intermediate container 115 holding the bulk intermediate medicament, where the intermediate container 115 is disposed in the housing and may be fluidically coupled to the activation mechanism 110. In alternative embodiments, a user may load the disposable injection device with the intermediate container 115 containing the bulk intermediate medicament, where the user may insert the intermediate container 115 into the injection device via an opening (capable of receiving a container and fluidically coupling the container to the activation mechanism) in the housing 105. Similarly, in another embodiment, a user may load the disposable injection device with a primary container 135 containing the mixture of the final medicament for injection purposes. For mixing purposes within the primary container 135, in some embodiments, a primary container may include a bulk intermediate medicament and a diluent that are stored separately until it is time for mixing.

In other embodiments, an intermediate container 115 may include a bulk intermediate medicament and a diluent stored separately, and the bulk intermediate medicament and the diluent are introduced to a primary container 130 for mixing. In yet another embodiment, an intermediate container 115 may include a bulk intermediate medicament and a diluent that are stored separately until it is time for mixing, where the mixing occurs in the intermediate container 115. The formed mixture may then be introduced to a primary container 130 for the injection process. In alternative embodiments the primary container 130 may include the diluent, and the intermediate container 115 includes the bulk intermediate medicament, and the diluent and bulk intermediate medicament are mixed in the primary container 130. The bulk intermediate medicament may be stored in form of a liquid medicament, dried medicament (powder, solid units, lyophilized, spray freeze dried, spray dried, and the like), solid medicament, or any combination thereof. In some embodiments, the wearable injection device may contain a bulk intermediate medicament in a primary container 130 or an intermediate container 115, while the user may load a diluent container 125 containing the diluent into the device. In alternative embodiments, the wearable injection device may contain the diluent, while the user may load an intermediate container 115 containing the bulk intermediate medicament into the device.

In an example embodiment, the activation mechanism 110 is an electromechanical mechanism comprising mechanical components and electrical components. The electromechanical activation mechanism may be, for example, a piezoelectric based system as discussed in detail below. A wearable injection device with an electromechanical activation mechanism may be a disposable injection device that may be preloaded with an intermediate container 115 containing a bulk intermediate medicament or that a user may load with an intermediate container 115 containing a bulk intermediate medicament. As described above, in some embodiments, the intermediate container 115 may store a bulk intermediate medicament and a diluent separately. Alternatively, the injection device may contain the bulk intermediate medicament, while the user may load a container containing the diluent into the device, or the injection device may contain the diluent, while the user may load an intermediate container 115 containing the bulk intermediate medicament into the device.

In some embodiments, the wearable injection device with an electromechanical activation mechanism may be a reusable injection device. The housing 105 of the reusable injection device is capable of receiving an intermediate container 115 containing a bulk intermediate medicament so a user can remove the old (used) container and load a new (unused) container to reuse the injection device. The housing 105 of the reusable injection device may have an opening on an outer surface of the housing, where the opening provides access to receive or remove a container. A user may load and unload the container from the housing 105 by inserting/pushing a container into the opening and by removing/pulling a container from the opening, respectively.

In some embodiments, the intermediate container 115 or primary container 130 may include a fluid path and a needle. The fluid path and the needle may be integrated in the container. Alternatively, the fluid path and needle may be provided as separate disposable components, for example, by a removably attachable means such as a luer fitting or pierced septum. The needle may be directly connected to the container via a rigid flow path or a flexible tube or catheter of suitable polymer or elastomer material.

For mixing purposes, the intermediate container 115 may contain a bulk intermediate medicament and a diluent that are stored separately within the container until it is time for mixing. Exemplary embodiments of the intermediate container for mixing are discussed below.

In some embodiments, the intermediate container 115 may be reusable so that the user loads the bulk intermediate medicament into the container before inserting it into the housing 105 of the injection device.

In an example embodiment, the activation mechanism 110 is an electrochemical activation mechanism consisting of electrical and chemical components. The electrochemical activation mechanism may include a chemical gas generator, for example, an expanding foam, that is in a non-expanded phase before administration of the medicament and that expands during administration to actuate a bung or a plunger forwardly within a barrel portion of a container (intermediate container 115 or primary container 130) disposed in the housing 105 of the wearable injection device. In other exemplary embodiments, the activation mechanism 110 may employ hydraulic pressure of working fluids, gas pressure of compressed gases, osmotic pressure, hydrogel expansion, electrochemical reaction solid state expansion, and the like to actuate the bung or the plunger.

An example electrochemical activation mechanism includes a battery. The battery may be an electrochemical cell whose expansion may be controlled by a microprocessor. When the battery is activated and discharges, the battery expands pushing a plunger included in the injection device and forcing the final medicament out of the housing 105 through the needle for injection into a patient. The battery may be disposed in the housing 105 and operatively connected to the primary container 130 or intermediate container 115 or mixing chamber 130 so that expansion of the battery causes the container or chamber to eject the final medicament via the injection needle. In some embodiments, the wearable injection device with an electrochemical activation mechanism may include a collapsible or deformable container for holding the final medicament, so that expansion of the battery causes the container to collapse and force the final medicament out of the injection device.

Another example chemical activation mechanism includes a phase stage driven expansion for driving a stopper or bung in the cartridge or syringe to eject the medicament. A gas such as butane or hexafluoroacetone (HFA) can be used in this embodiment. The gas may be disposed at one end of the injection device, for example, a distal end that is furthest away from the patient.

Medicament Container

In some embodiments, the wearable injection device may include an intermediate container holding the bulk intermediate medicament within the housing. In other embodiments, the wearable injection device is configured to receive an intermediate container holding the bulk intermediate medicament or a primary container holding a final medicament.

Each of the intermediate container and primary container includes a barrel portion that is used to store a bulk intermediate medicament or final medicament. The barrel portion may be pre-filled with the bulk intermediate medicament. The barrel portion may be pre-filled with a bulk intermediate medicament by a manufacturer prior to distribution or sale. In an example embodiment, the intermediate container may be prefilled with a bulk intermediate medicament and a diluent, and they may be stored separately in the intermediate container. In some embodiments, the barrel portion may be filled by a user. As discussed above, the intermediate container and primary container may be a cartridge or a syringe. A needle may be coupled to the cartridge. The syringe may be a dual or multi-chamber syringe that is pre-filled with the medicament (active drug and diluent).

Exemplary barrel portions may be formed of any suitable material including, but not limited to, a polymer material (e.g., a medical grade polymer), metal, glass, thermoplastic, elastomers, silicone crystals, and the like. In an exemplary embodiment, the barrel portion may be rigid or may take the form of one or more flexible pouches for holding the final medicament or the bulk intermediate medicament.

As shown in FIG. 15, the housing of the wearable injection device may include a plurality of cartridges 1502, syringes 1504, or vials 1506, in any combination. Alternatively, the wearable injection device may receive a plurality of cartridges, syringes, vials, or contents of vials, in any combination.

Exemplary embodiments described herein with reference to a syringe may also be implemented using a cartridge or a vial. Similarly, exemplary embodiments described herein with reference to a cartridge may also be implemented using a syringe or a vial.

In some embodiments, the intermediate container stores a bulk intermediate medicament and diluent separately, and is configured to mix them to form a mixture prior to injection. Exemplary containers are capable of holding a volume of mixture (e.g., final medicament) ranging from 0.1 milliliters to 10 milliliters. Exemplary wearable injection devices are capable of ejecting a mixture/final medicament having a viscosity ranging from 1 centipoise (cP) to 50 centipoise (cP).

Figure 13:
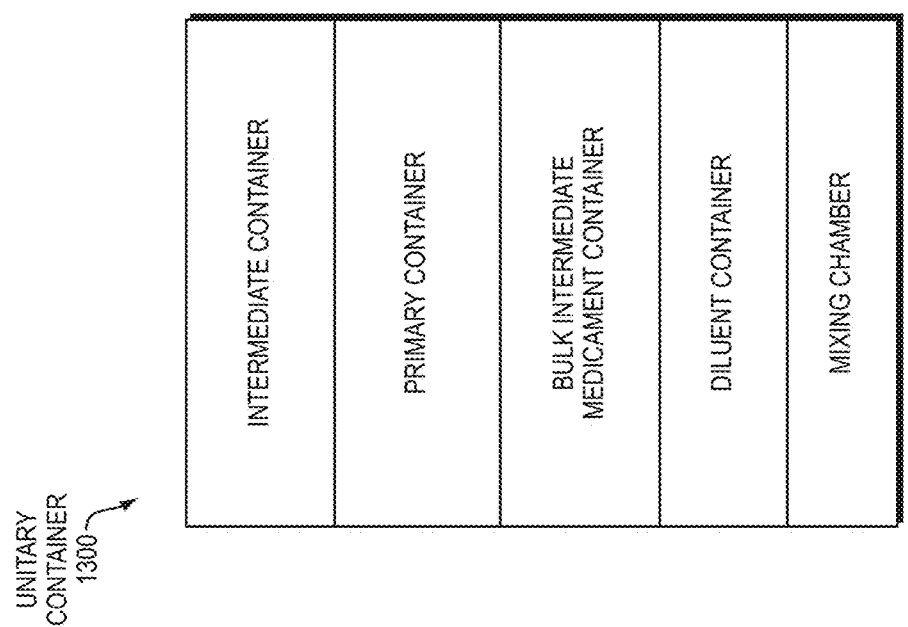
FIG. 13 illustrates a container for exemplary embodiments of the wearable injection device, according to an example embodiment.

Exemplary embodiments of the wearable injection device include and describe an intermediate container, a primary container, a diluent container, a bulk intermediate container, a mixing chamber, or a combination thereof. In some embodiments, all of the containers and the mixing chamber may be provided as a single container or a unitary container as shown in the description of the embodiments. As shown in FIG. 13, the unitary container 1300 includes the intermediate container, the primary container, the bulk intermediate medicament container, the diluent container, and the mixing chamber.

FIG. 14 illustrates an example embodiment of the injection assembly 120 described in relation to FIGS. 1A, 1B, and 1C. The injection assembly 120 includes the delivery cannula 1406, and may include a plunger 1402 and a bung 1404. In an alternate embodiment, the plunger 1402 and the bung 1404 are included in the container 1408. As described above, the delivery cannula 1406 is in fluid communication with the container 1408 containing the final medicament, which may be the intermediate container 115, the primary container 135, or the mixing chamber 130 as described in various embodiments above. The delivery cannula 1406 and the container 1408 are in fluid communication via fluid pathway 1410. The fluid pathway 1410 may be formed via a fluid conduit. In some embodiments, the injection assembly 120 includes a biasing mechanism to extend and retract the injection needle.

Mixing Mechanisms/Mixing Chambers

Exemplary mixing mechanisms or chambers that may be used in exemplary wearable automatic injection devices are described with reference to FIGS. 4-13. Some of the exemplary embodiments also include mechanisms for separately storing a bulk intermediate medicament in dry or liquid form and a diluent in liquid form. Some bulk intermediate medicaments are stored in dried form, such as a powder or solid unit form because they are more stable in a dried form. For some routes of administration, such bulk intermediate medicaments may need to be mixed or reconstituted with a liquid or diluent before they can be administered. Reconstitution of a drug involves mixing the bulk intermediate medicament in dry form with the diluent to form a mixture to be injected into a patient. Mixing, for example to reconstitute a bulk intermediate medicament, may require rigorous mixing or agitation of the diluent and the bulk intermediate medicament to form a final medicament. For some bulk intermediate medicaments complete reconstitution is not necessary, and mere/slight mixing of the drug particles with a liquid is enough for injection. In this case, the liquid is responsible for carrying the bulk intermediate medicament particles through the injection needle into the patient's skin and bloodstream, and full reconstitution may take place in the patient or may be absorbed by the patient.

Exemplary mixing mechanisms may be included in the intermediate container 115a described in relation to FIG. 1A, the mixing chamber 130b described in relation to FIG. 1B, and the mixing chamber 130c described in relation to FIG. 1C.

Figure 2A:
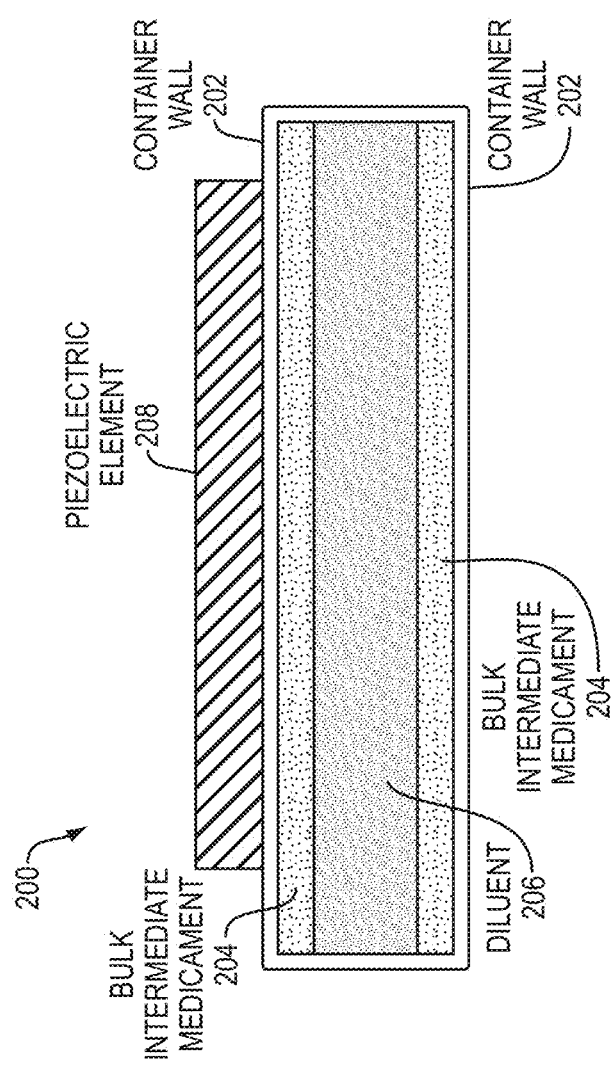
FIG. 2A illustrates a mixing mechanism with a piezoelectric element, according to an example embodiment.

FIG. 2A illustrates an exemplary embodiment of the intermediate container 115 that also serves as the mixing chamber 130, and in some embodiments also serves as the primary container 135. The container 200 includes a piezoelectric mixing element 208. In this embodiment, a bulk intermediate medicament 204 is applied to the inner surface of a container wall 202, and a diluent 206 is disposed in the container. The piezoelectric element 208 is disposed on an outer surface of the container wall 202. The piezoelectric element 208 may circumferentially extend completely around the outer container wall, or may circumferentially extend partially around the outer container wall, for example, 60°, 90°, 120°, etc. In some embodiments, a plurality of piezoelectric elements 208' are circumferentially spaced about the outer wall of the container 250, as shown in FIG. 2A. In some embodiments, the plurality of piezoelectric elements 208 abut each other, and in some embodiments they are spaced apart. The bulk intermediate medicament 204 may be applied to the inner surface of the container wall 202 so that a layer of drug is disposed or coupled to the inner surface of the container wall 202. In some embodiments, an adhesive is used that does not interfere with the bulk intermediate medicament 204. The bulk intermediate medicament 204 may be applied to the wall such that the bulk intermediate medicament 204 stays on the wall during any transport of the container 200 or transport of the wearable injection device, and the bulk intermediate medicament 204 releases from the wall when the piezoelectric element 208 is activated.

As discussed above, the container 200 may be a cartridge or a syringe. The container 200 may be coupled to a needle as well. The container may be prefilled by the manufacturer or the pharmacy with the bulk intermediate medicament coated on the inner surface of the container wall 202 and the diluent disposed in the container 200. The diluent 206 may be filled in the container 200 using any suitable methods so that the bulk intermediate medicament coating on the inner surface of the container 200 is not disturbed. The diluent 206 may be any liquid or fluid required to mix the bulk intermediate medicament 204. The type and amount of diluent 206 may be dictated by the type and amount of bulk intermediate medicament 204, which may be dictated by the treatment the wearable injection device aims to provide. The manufacturer of the drug may also dictate the amount and type of the diluent required to reconstitute the bulk intermediate medicament.

The piezoelectric element 208 may be disposed on an outer surface of the container wall 202 using any suitable means, for example, an adhesive. In some embodiments, the piezoelectric element 208 is attached or coupled to the container wall 202, while in other embodiments, the piezoelectric element 208 is adjacent to the container and not actually touching the wall. The piezoelectric element 208 can be a piezoelectric motor that produces acoustic or ultrasonic vibrations to cause linear or rotary motion within the container 200. The piezoelectric element 208 is connectable to a source of power and in some embodiments a driver mechanism or circuit. In some embodiments, a sound energy is applied to the container 200 such as cavitating ultrasound to disperse or dissolve the bulk intermediate medicament 204 into the diluent 206. As discussed above, the bulk intermediate medicament 204 is deposited on the inner surface of the container wall (in form of a powder, a film, or a coating). In some embodiments, at time of mixing, the container walls are induced to vibrate ultrasonically. In some embodiments, the ultra-sound energy induces high local differential pressures in the bulk intermediate medicament 204 coating via diluent cavitation. The cavitation etches the bulk intermediate medicament enhancing dissolution and dispersion of the bulk intermediate medicament into the diluent.

When the piezoelectric element 208 is activated or energized by a power source (not shown), it causes the bulk intermediate medicament 204 to release from the container wall 202 into the diluent 206. The piezoelectric element 208 may remain active until the bulk intermediate medicament and diluent are mixed well and reconstituted. Activation of the exemplary activation mechanism 110 discussed above may trigger activation and deactivation of the piezoelectric element 208. The piezoelectric element 208 may be deactivated after a specific predetermined period of time that may be configurable by the manufacturer or the user. Alternatively, the activation and deactivation of the piezoelectric element 208 may be controlled by the user via the actuation button 165 associated with the activation mechanism 110 provided on the wearable injection device. For example, the user may press the actuation button 165 to start the piezoelectric element 208 to initiate the mixing process prior to the injection, and press the actuation button 165 again to stop the piezoelectric element 208 when the user determines that the bulk intermediate medicament 204 is mixed (using the inspection window 160 for example). Alternatively, the piezoelectric element 208 may be automatically deactivated when the wearable injection device determines that the mixing is complete (using a turbidity meter for example). The piezoelectric element 208 may cause cavitation within the container 200. In some embodiments, the piezoelectric element 208 may produce an ultra-sonic wave for sonication.

In some embodiments, there may be an additional layer of material disposed on top the bulk intermediate medicament 204 between diluent 206 and bulk intermediate medicament 204. The additional layer may be made of a material that allows for the drug to pass through when the piezoelectric element is active, but prevents the diluent from passing through.

In an example embodiment, instead of a piezoelectric mixing element, the container 200 may include any other electrical or mechanical displacement actuator, such as a rotary or linear motor, electromagnetic vibrating mechanism, or the like. In another embodiment, the container 200 may include any other electrical or mechanical displacement actuator in addition to the piezoelectric mixing element.

Figure 2B:
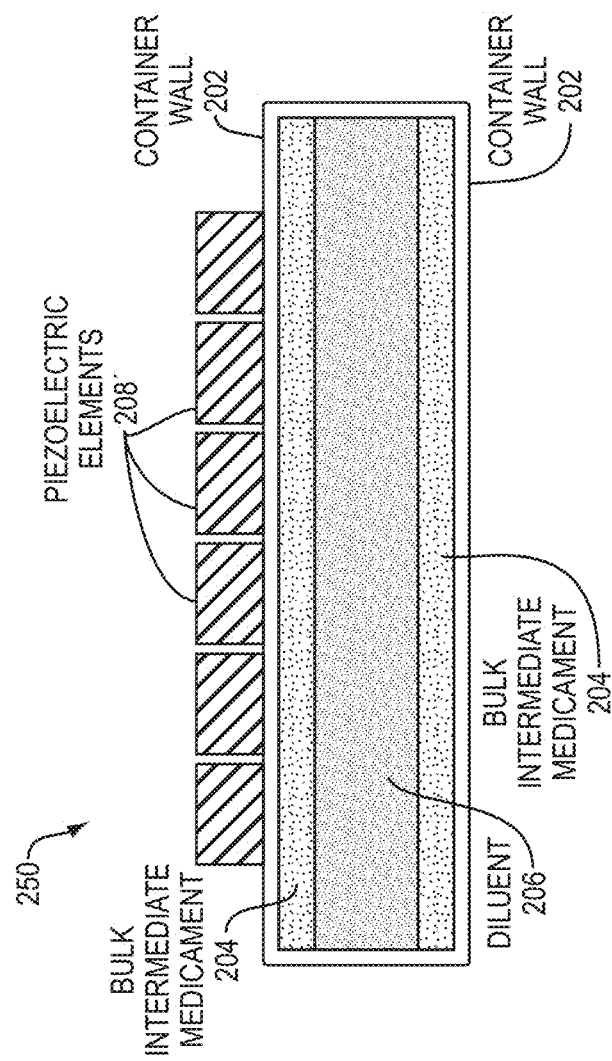
FIG. 2B illustrates a mixing mechanism with multiple piezoelectric elements, according to an example embodiment.

In some embodiments, the system illustrated in FIGS. 2A and 2B is provided outside of the wearable injection device. This embodiment allows the wearable injection device to be reused as the user can mix the final medicament externally, and insert the container in the injection device. In this case, the container 200 is provided to the user with the piezoelectric element 208 removably disposed on it. The container 200 is provided to the user separately from the wearable injection device. These components may be provided in a mixing housing (separate from the wearable injection device, illustrated as the mixing mechanism 140c in FIG. 1C). The user can actuate the activation button 166c on the mixing housing to start the piezoelectric element 208. The vibrations from the piezoelectric element 208 causes the bulk intermediate medicament 204 to release from the container wall 202 into the diluent 206. Once reconstitution or mixing is complete, the user can actuate the activation button 166c again to stop the piezoelectric element 208. The user can then remove the container 200 from the mixing housing and place it in the wearable injection device (illustrated as the housing 105c in FIG. 1C). In some embodiments, the piezoelectric element 208 is removable from the container 200. With a removable piezoelectric element the user can remove it (for example, by pulling on it), and then insert the container 200 into the wearable injection device. In this embodiment, the mixing housing may also contain mechanisms to verify reconstitution of the bulk intermediate medicament automatically or manually. For example, the mixing housing of the wearable injection device may include the turbidity meter 155c to sense the cloudiness of the mixture, and the housing 105c may include the inspection window 160c for the user to visually inspect the cloudiness of the mixture.

After the mixing process is complete, the mixture in the container 200 is ready for the injection process. The container 200 is fluidically coupled to the activation mechanism 110 and the injection assembly 120 (discussed above) in the housing 105 of the wearable injection device to inject the patient with the final medicament.

FIG. 2B illustrates an exemplary embodiment of an intermediate container that also serves as a mixing container, and in some embodiments also serves as the primary container. The container 250 includes multiple piezoelectric elements 208'. The container 250 includes similar components as the container 200 described in relation to FIG. 2A, and also performs the similar operations and functions.

Figure 3:
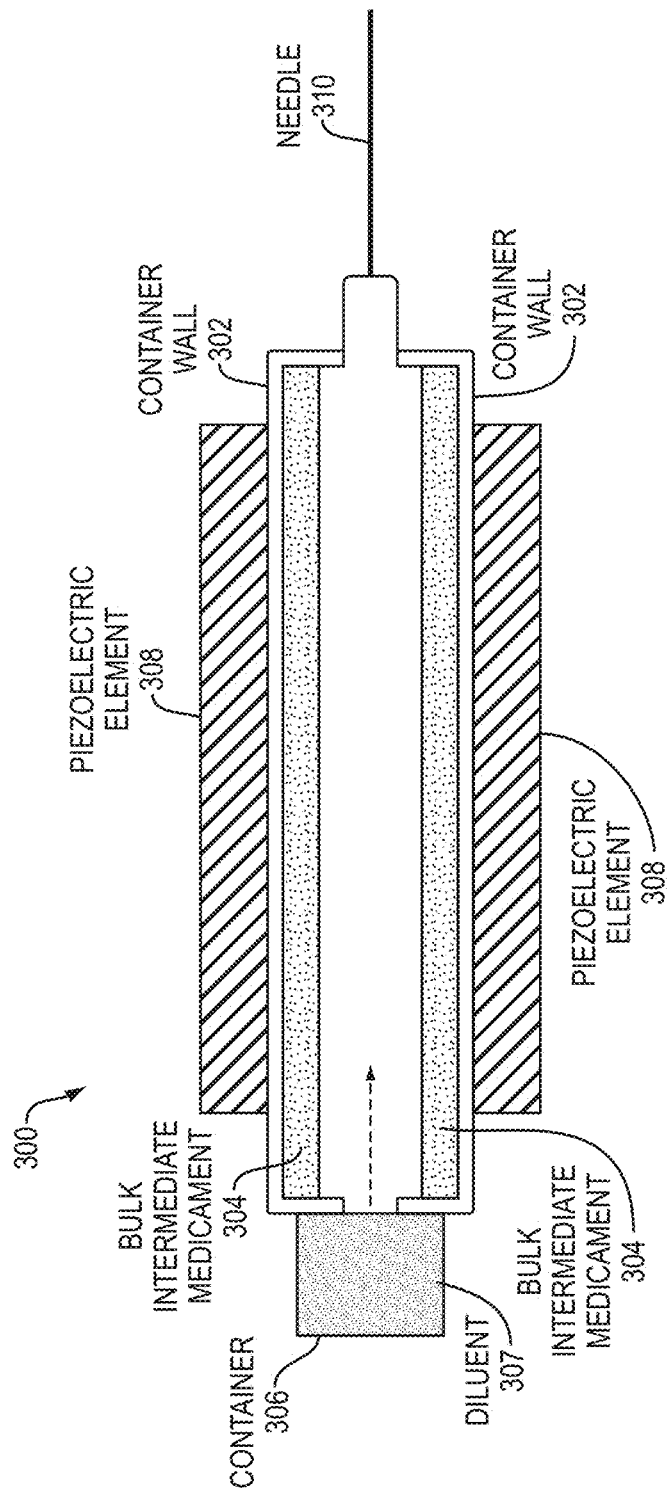
FIG. 3 illustrates a mixing mechanism with a piezoelectric element, according to an example embodiment.

FIG. 3 illustrates another exemplary embodiment of a mixing mechanism with a piezoelectric mixing element. In this embodiment, a container 300 includes a bulk intermediate medicament 304 applied to the inner surface of a container wall 302, and a diluent 307 is provided outside of the container in a separate diluent container 306 as illustrated. A piezoelectric element 308 is disposed on an outer surface of the container wall 302. In some embodiments, two piezoelectric elements 308 are disposed on an outer surface of the container wall 302. The piezoelectric element 308 may circumferentially extend completely around the outer container wall, or may circumferentially extend partially around the outer container wall, for example, 60°, 90°, 120°, etc. In some embodiments, a plurality of piezoelectric elements 308 are circumferentially spaced about the outer wall of the container 300. In some embodiments, the plurality of piezoelectric elements 308 abut each other, and in some embodiments they are spaced apart.

The bulk intermediate medicament 304 may be applied to the container wall 302 so that a layer of bulk intermediate medicament is disposed on or coupled to the inner surface of the container wall 302. In some embodiments, an adhesive is used that does not interfere with the bulk intermediate medicament 304. The bulk intermediate medicament 304 may be applied to the inner surface of the container wall 302 such that the bulk intermediate medicament stays on the wall during any transport of the container 300 or transport of the wearable injection device, and the bulk intermediate medicament 304 releases from the inner surface of the container wall 302 when the piezoelectric element 308 is activated. The container 300 can also be coupled to a needle 310. The container may be prefilled by the manufacturer or pharmacy with the bulk intermediate medicament coated on the inner surface and the diluent disposed in the separate diluent container 306.

In this embodiment, the diluent 307 is provided in a diluent container 306 separate from the container 300. The diluent 307 passes through the container during the reconstitution process. The diluent 307 may be any liquid or fluid required to reconstitute or mix the drug. The type and amount of diluent 307 may be dictated by the type and amount of bulk intermediate medicament 304, which may be dictated by the treatment the wearable injection device aims to provide. The manufacturer of the drug may also dictate the amount and type of the diluent required to reconstitute the bulk intermediate medicament.

The piezoelectric element 308 may be disposed on outer surface of the container wall 302 using any suitable means, for example, an adhesive. In some embodiments, the piezoelectric element 308 is removably coupled to the container wall 302. The piezoelectric element 308 can be a film that produces acoustic or ultrasonic vibrations to cause linear or rotary motion. The piezoelectric elements 308 are connectable to a source of power and in some embodiments to a driver mechanism or circuit.

When the piezoelectric element 308 is activated or energized by a power source (not shown), it causes the bulk intermediate medicament 304 to release from the container wall 302 into the diluent 307 that is introduced into the container 300 from diluent container 306. The diluent 307 may pass through the container 300 during the injection process, thus, the mixing and injection process occur simultaneously. During the injection process, the diluent 307 may be pumped into the container 300 using a plunger, and the piezoelectric element 308 releases the bulk intermediate medicament 304 into the diluent 307. The piezoelectric element 308 may remain active until the bulk intermediate medicament 304 and diluent 307 are mixed well and reconstituted. Actuation of the exemplary activation mechanism discussed above may trigger activation and deactivation of the piezoelectric element 308. The piezoelectric element 308 may be deactivated after a specific period of time that may be configurable by the manufacturer or the user. Alternatively, the activation and deactivation of the piezoelectric element 308 may be controlled by the user via an actuation button 165, associated with the activation mechanism 110, provided on the wearable injection device. For example, the user may press the actuation button 165 to start the piezoelectric element to initiate the mixing process prior to injection, and press the actuation button 165 again to stop the piezoelectric element when the user determines that the bulk intermediate medicament is reconstituted (using an inspection window for example). Alternatively, the piezoelectric element 308 may be automatically deactivated when the wearable injection device determines that the reconstitution is complete (using a turbidity meter for example). The piezoelectric element 308 may cause cavitation with in the container 300. In some embodiments, the piezoelectric element 308 may produce an ultra-sonic wave for sonication.

In some embodiments, a sound energy is applied such as cavitating ultrasound to disperse or dissolve the bulk intermediate medicament 304 into the diluent 307. As discussed above, the bulk intermediate medicament 304 is deposited on the inner surface of the container wall 302 (in form of a powder, a film, or a coating). In some embodiments, upon introduction of the diluent 307, the container walls 302 are induced to vibrate ultrasonically. In some embodiments, the ultra-sound energy induces high local differential pressures in the bulk intermediate medicament coating via diluent cavitation. The cavitation etches the bulk intermediate medicament 304 enhancing dissolution and dispersion of the bulk intermediate medicament 304 into the diluent 307.

In some embodiments, there may be an additional layer of material disposed on top the bulk intermediate medicament 304 between diluent 307 and bulk intermediate medicament 304. The additional layer may be made of a material that allows for the drug to pass through when the piezoelectric element is active, but prevents the diluent from passing through.

In an example embodiment, instead of a piezoelectric mixing element, the container 300 may include any other electrical or mechanical displacement actuator, such as a rotary or linear motor, electromagnetic vibrating mechanism, or the like. In another embodiment, the container 300 may include any other electrical or mechanical displacement actuator in addition to the piezoelectric mixing element.

After the mixing process is complete, the mixture in the container 300 is ready for the injection process. The container 300 is fluidically coupled to the activation mechanism 110 and the injection assembly 120 (discussed above) in the housing 105 of the wearable injection device to inject the patient with the final medicament.

Figure 4:
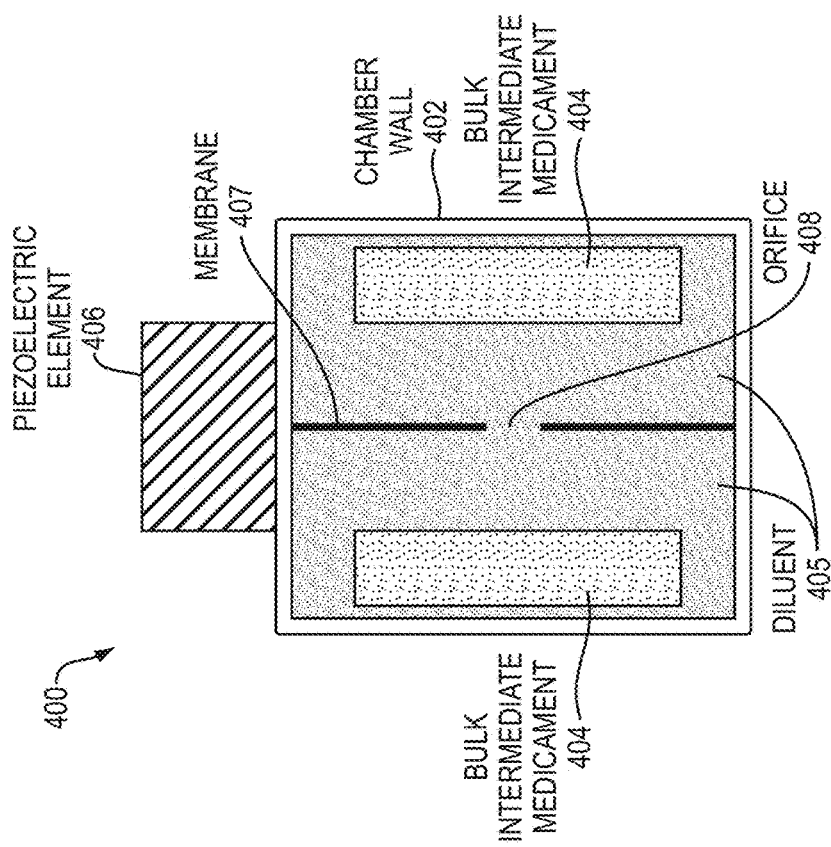
FIG. 4 illustrates a mixing mechanism with a piezoelectric element, according to an example embodiment.

FIG. 4 illustrates another exemplary embodiment of a chamber 400 with a piezoelectric element. In this embodiment, a bulk intermediate medicament 404 is applied to the inner surface of the chamber wall 402 of a chamber 400. A piezoelectric element 406 is disposed on an outer surface of the chamber wall 402 of the chamber 400. The chamber 400 further includes a membrane 407 having an orifice 408. The bulk intermediate medicament 404 may be applied to the inner surface of the chamber wall 402 so that a layer of bulk intermediate medicament 404 is disposed on or coupled to the chamber wall 402. In some embodiments, an adhesive is used that does not interfere with the medicament. The bulk intermediate medicament 404 may be applied to the inner surface of the chamber wall 402 such that the bulk intermediate medicament stays on the surface during any transport of the chamber 400 or transport of the wearable injection device, and the bulk intermediate medicament 404 releases from the surface when the piezoelectric element 406 is active. The chamber 400 may be prefilled by the manufacturer or pharmacy with the bulk intermediate medicament 404 coated on the inner surface of the chamber wall 402 and a diluent 405 disposed in the chamber 400. In some embodiments, the diluent 405 may be introduced into the chamber 400 during the mixing process.

The piezoelectric element 406 vibrates the membrane 407 with the orifice 408. In some embodiments, the membrane 407 may include more than one orifice. The orifice 408 of membrane 407 operates in conjunction with the piezoelectric element 406 and the diluent 405 to form a synthetic jet flow. The synthetic jet flow is made up of the surrounding diluent 405, and is formed by flow moving back and forth through the small orifice 408. The synthetic jet is produced by periodic ejection and suction of fluid from the orifice 408. The synthetic jet flow aids in mixing the bulk intermediate medicament 404 released from the inner surface of the chamber wall 402 of the chamber 400. There is no effective transfer of mass with the use of an orifice in this embodiment.

The piezoelectric element 406 may be disposed on an outer surface of the chamber 400 using any suitable means, for example, an adhesive. In some embodiments, the piezoelectric element 406 is permanently attached or removably coupled to the chamber 402. The piezoelectric element 406 can be a piezoelectric motor that produces acoustic or ultrasonic vibrations to cause linear or rotary motion.

When the piezoelectric element 406 is activated or energized by a power source (not shown), it causes the bulk intermediate medicament 404 to release from the chamber wall 402, either by itself or in combination with the diluent 405. In an example embodiment, the diluent 405 is introduced into the chamber 400 forming a synthetic jet flow via the orifice 408. The piezoelectric element 406 may remain active until the bulk intermediate medicament 404 and diluent 405 are mixed well and reconstituted. Actuation by the user of an exemplary activation mechanism discussed above may trigger activation and deactivation of the piezoelectric element 406. The piezoelectric element 406 may be deactivated after a specific period of time that may be configurable by the manufacturer or the user. Alternatively, the activation and deactivation of the piezoelectric element 406 may be controlled by the user via an actuation button 165, associated with the activation mechanism 110, provided on the wearable injection device. For example, the user may press the actuation button 165 to start the piezoelectric element to initiate the reconstitution process prior to injection, and press the actuation button 165 again to stop the piezoelectric element when the user determines that the bulk intermediate medicament 404 is reconstituted (using the inspection window 160 for example). Alternatively, the piezoelectric element 406 may be automatically deactivated when the wearable injection device determines that the reconstitution is complete (using the turbidity meter 155 for example). The piezoelectric element 406 may cause cavitation within the chamber 400. In some embodiments, the piezoelectric element 406 may produce an ultra-sonic wave for sonication.

In some embodiments, the membrane 407 may be initially sealed, but rupturable by application of pressure from the piezoelectric element 406 allowing the diluent 405 and bulk intermediate medicament 404 to mix. The synthetic jet flow may be bidirectional to allow for mixing between the compartments.

In some embodiments, there may be an additional layer of material disposed on top of the bulk intermediate medicament 404 coating on the inner surface of the chamber wall 402 of the chamber 400. The additional layer may be made of a material that allows for the bulk intermediate medicament 404 to pass through when the piezoelectric element is active, but prevents the diluent 405 from passing through.

In an example embodiment, instead of a piezoelectric mixing element, the container 400 may include any other electrical or mechanical displacement actuator, such as a rotary or linear motor, electromagnetic vibrating mechanism, or the like. In another embodiment, the container 400 may include any other electrical or mechanical displacement actuator in addition to the piezoelectric mixing element.

After the reconstitution or mixing process is complete, the mixture in the chamber 400 is ready for the injection process. The chamber 400 is fluidically coupled to primary container 130, or directly to the activation mechanism 110 and the injection assembly 120 (discussed above) in the housing 105 of the wearable injection device to inject the patient with the final medicament.

Figure 5:
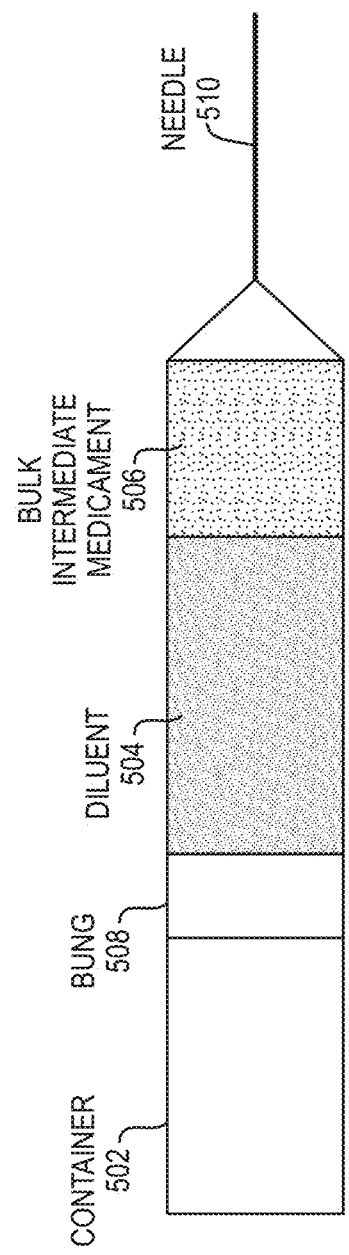
FIG. 5 illustrates a mixing mechanism with a porous element, according to an example embodiment.

FIG. 5 illustrates an exemplary embodiment of a dual chamber container 502 with a porous element. In this embodiment, a porous element 506 is disposed at a first end (for example, proximal end that is closest to the patient) of the container 502, and a bung 508 is disposed at a distal end of the container 502. A diluent 504 is disposed in the container 502. The container 502 can be coupled to a needle 510. The porous element 506 includes the bulk intermediate medicament. The bung 508 is used to force the diluent 504 through the porous element 506 causing mixing of the diluent 504 and the bulk intermediate medicament to form a mixture. Upon activation of the activation mechanism 110, for example, via the button 165, the bung 508 may be moved within the container 502 using a plunger. The mixture may be ejected from the container 502 through needle 510. In some embodiments, the container 502 includes an orifice, a luer lock, or a septum instead of needle 510, and the mixture is ejected through the orifice, luer lock or septum.

The porous element 506 is made in a generally matrix form comprising many interstices that can be filled with a bulk intermediate medicament in dried form, such as a powder or solid units. In some embodiments, the porous element 506 is coated with the bulk intermediate medicament that may be in powder, solid, or liquid form, and then the porous element 506 is dried to incorporate the bulk intermediate medicament into the porous element 506. The porous element 506 may include milliliters or milligrams of bulk intermediate medicament. The porous element 506 may be made of ceramic, polymer, carbon, glass, any other suitable material, or any combination thereof. The bulk intermediate medicament may be a dried medicament (powder, solid units, lyophilized, spray freeze dried, spray dried, and the like). The diluent 504 is forced through the porous element 506 releasing the bulk intermediate medicament contained therein into the diluent 504. The resulting mixture is then injected into the patient. The bung 508 can be used to move the diluent 504 forward through the porous element 506. In alternative embodiments, any other means can be used to force the diluent 504 through the porous element 506.

In some embodiments, the bung 508 is also used to eject the mixture through needle 510, and inject the patient with the mixture. In some embodiments, movement of the bung 508 ceases after the diluent 504 has passed through the porous element 506. In an example embodiment, there is a layer provided between the diluent 504 and porous element 506 so that the diluent does not pass through the porous element until a certain amount of force is applied to move the diluent, and does not mix with the bulk intermediate medicament based on transport of the container or the wearable injection device.

After the reconstitution or mixing process is complete, the mixture in the container is ready for the injection process. The container is fluidically coupled to the activation mechanism 110 and the injection assembly 120 (discussed above) in the housing 105 of the wearable injection device to inject the patient with the final medicament.

Figure 6:
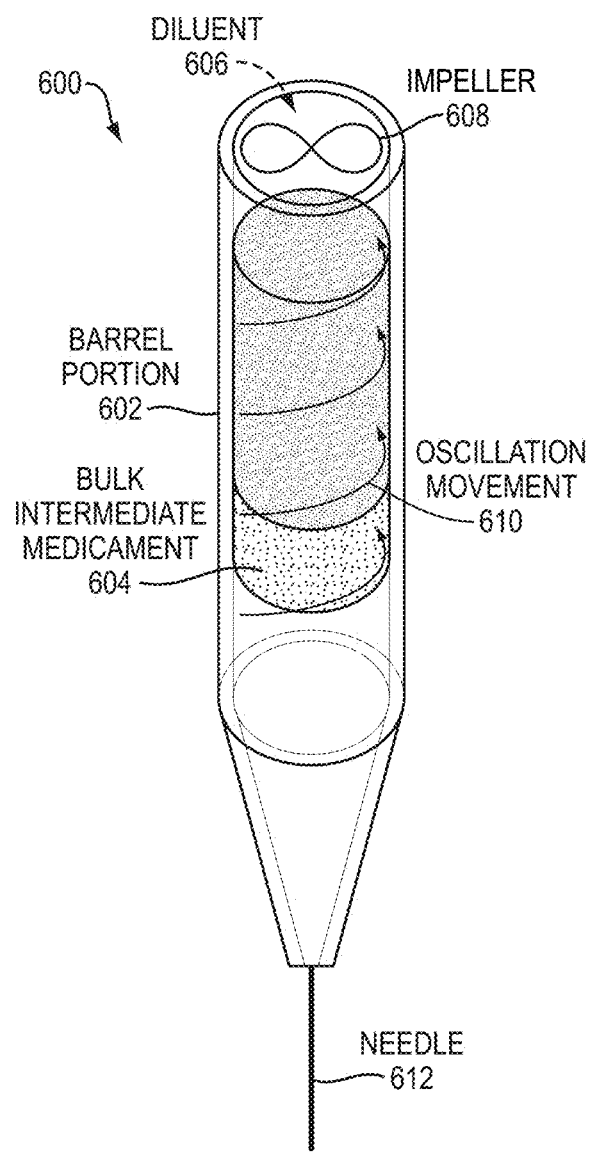
FIG. 6 illustrates a mixing mechanism using an oscillator, according to an example embodiment.

FIG. 6 illustrates an exemplary embodiment of an intermediate container 600 including an impeller that induces helical flow. A bulk intermediate medicament 604 is disposed at a first end (for example, a proximal end that is closest to the patient) of a barrel portion 602 of the container 600. An impeller 608 is disposed in or coupled to the barrel portion 602. Diluent 606 is introduced into the barrel portion 602. A needle 612 may be coupled to the barrel portion 602. The bulk intermediate medicament 604 may be disposed at the proximal end in a dried form (powder, solid units, lyophilized, spray freeze dried, spray dried, and the like), and may be packed at the proximal end so that the bulk intermediate medicament 604 does not move around within the barrel portion 602. Alternatively, the bulk intermediate medicament 604 may be disposed in the barrel portion without any mechanism to prevent it from moving around in the barrel portion. The container 600 may be prefilled by the manufacturer or pharmacy with the bulk intermediate medicament 604, and the diluent 608 may be provided in a separate vessel. Alternatively, the bulk intermediate medicament 604 and diluent 608 may be loaded by the user into the barrel portion 602 of the container 600.

The impeller 608 can be any mechanical, electrical, electromechanical, chemical, and/or electrochemical driven that can produce helical or oscillation movement within the barrel portion 602 when the diluent 606 is introduced. The oscillation movement (illustrated by arrows 610) is repetitive movement in the barrel portion 602 that aids in mixing the diluent 606 and bulk intermediate medicament 604 to create a mixture. In some embodiments, the container 600 includes a vent or valve to allow for gas to escape before the mixture is ejected into a patient. The impeller 608 may be activated by the activation mechanism 110, for example, by actuation of the button 165.

The barrel portion 602 of the container 600 may be provided in the wearable injection device by a manufacturer prior to distribution, or the barrel portion 602 may be provided separately from the wearable injection device and the user can load it into the wearable injection device after mixing is complete. After the mixing process is complete, the mixture in the container 600 is ready for the injection process. The container 600 is fluidically connected to the activation mechanism 110 and the injection assembly 120 (discussed above) in the housing 105 of the wearable injection device to inject the patient with the final medicament.

Figure 7:
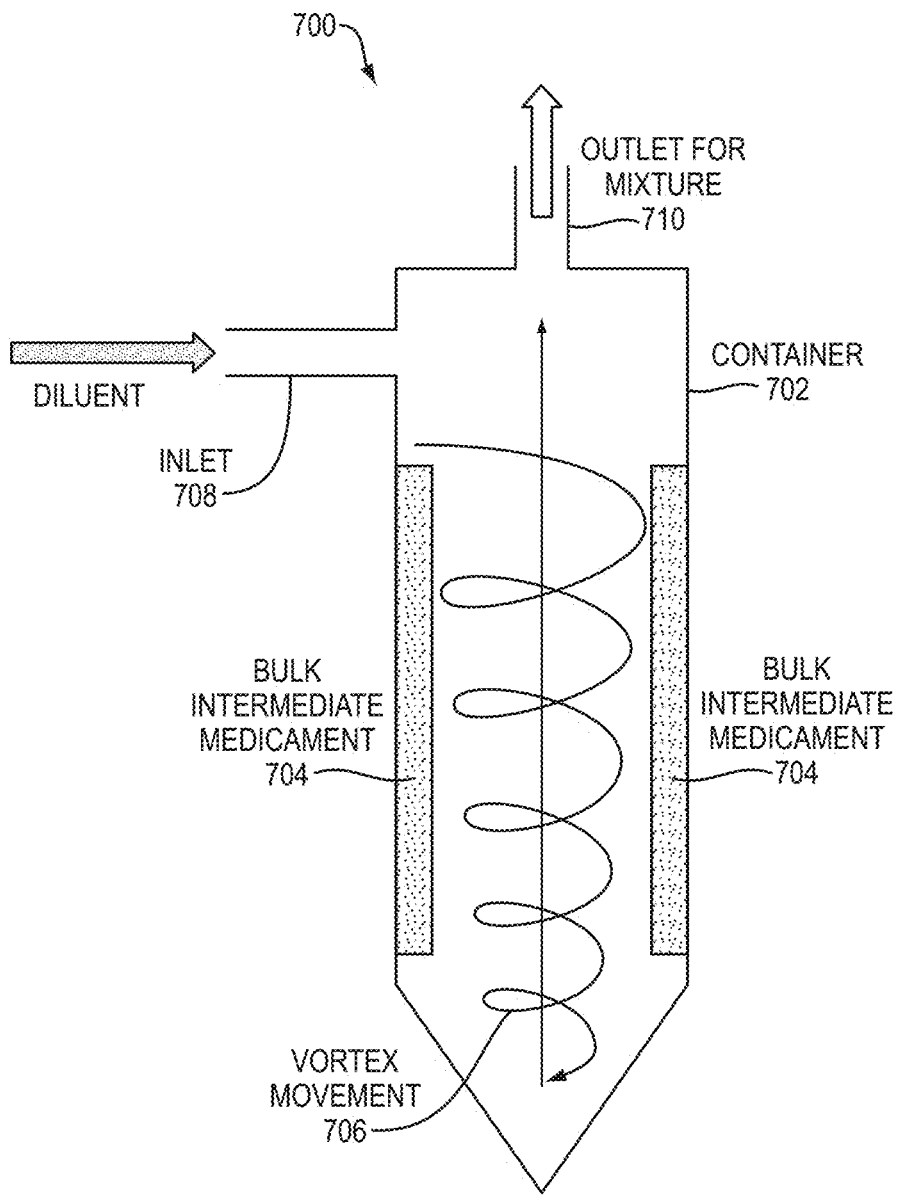
FIG. 7 illustrates a mixing mechanism using a vortex generator system, according to an example embodiment.

FIG. 7 illustrates an exemplary embodiment of an intermediate container 700 configured as a vortex generation system. In this embodiment, the agitation mechanism is configured as and operable as a centrifugal separator (CS) or a vortex generator (VG) system to mix the bulk intermediate medicament and diluent. The container 702 contains bulk intermediate medicament 704, for example in a dried form (powder, solid units, lyophilized, spray freeze dried, spray dried, and the like). The bulk intermediate medicament 704 may be freely disposed in the container 702, or the bulk intermediate medicament 704 may be applied (via a layer coating) on an inner surface of the container 702 using, for example, a suitable adhesive or other means. The bulk intermediate medicament 704 may be pre-filled by a manufacturer or pharmacy. The diluent is tangentially introduced to the container 702 via inlet 708. The diluent may be provided in a separate vessel. The diluent may be introduced to the container 702 upon activation of the activation mechanism 110, for example, via the button 165. The overall geometry of the container 702 accelerates the diluent 712, as shown by arrow 706, within the container 702. The vortex movement of the diluent allows for the diluent and bulk intermediate medicament to mix. The diluent can scour or scrap the bulk intermediate medicament from the inner surface of the container 702 via the vortex movement.

The vortex initially accelerates the flow in a vortex flow pattern downwardly towards a conically shaped terminal end of the container 702. The vortex flow pattern increases the shear gradient on the walls of the barrel portion, which improves separation and release of bulk intermediate medicament 704 from the wall, and keeps large drug particles centrifugally confined to the walls until it dissolves in the diluent. The mixture is withdrawn axially through outlet 710. The outlet 710 is designed so that small or minute particles make it through. The vortex movement in the container 702 may be generated using any type of impeller rotor that drives the container 702 system to accelerate the diluent 712 outwards from the center of rotation. In some embodiments, no impeller is needed; the structure of the container 702 itself creates the vortex flow pattern to mix the diluent and the bulk intermediate medicament. In this embodiment, the diluent 712 is pressurized as it enters the container 702. As the container 702 fills, mixing of the diluent 712 and bulk intermediate medicament 704 occurs to create the final medicament. In an example embodiment, the inlet 708, the outlet 710, and the shape of the container 702 can be designed to influence flow and mixing patterns within the container 702.

Once the bulk intermediate medicament 704 is mixed with the diluent, the resulting mixture is withdrawn from the container 702. In example embodiments, the mixture (the final medicament) is withdrawn into a primary container disposed in the wearable injection device or to be inserted into the wearable injection device. In exemplary embodiments, the CS/VG system is provided separately from the wearable injection device. In alternative embodiments, the CS/VG system is provided within the wearable injection device. The CS/VG system may be reusable where the user is able to load the bulk intermediate medicament into the CS/VG system.

Figure 8:
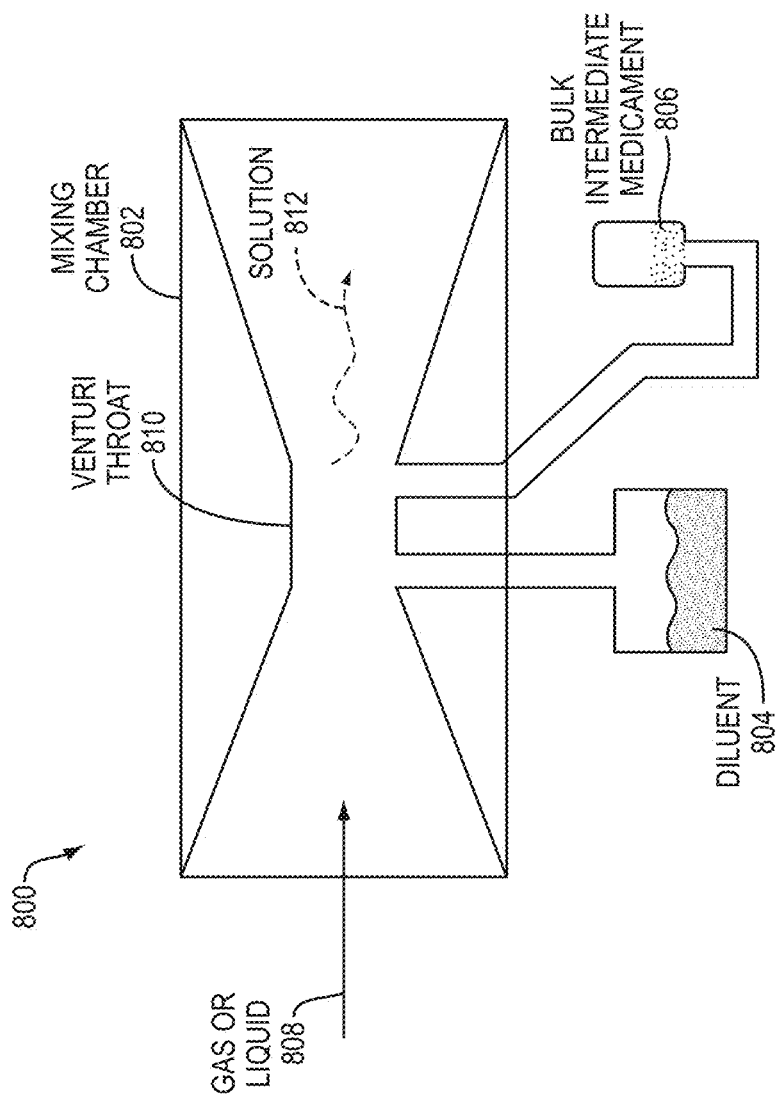
FIG. 8 illustrates a mixing mechanism using a Venturi-effect system, according to an example embodiment.

FIG. 8 illustrates an exemplary embodiment of a mixing chamber 802 configured with a restricted fluid pathway and operable to take advantage of the Venturi-effect. The Venturi-effect is the reduction in fluid pressure resulting from the fluid flowing through a constricted or narrower section of a fluid pathway. The velocity of the fluid increases as the cross-section of the structure decreases. The Venturi system 800 includes a container containing diluent 804, a container containing bulk intermediate medicament 806, and a mixing chamber 802 having a venturi throat 810. The mixing chamber 802 may have a tubular structure having a section with a narrowed cross-section or constricted section to form the venturi throat 810. A fluid (gas or liquid) is introduced from distal end 808. The fluid may be introduced upon activation of the activation mechanism 110, for example, via actuation of the button 165. The fluid may be the diluent in some embodiments, and the container 804 may contain a second bulk intermediate medicament to be reconstituted. The bulk intermediate medicament may be contained in dried form (powder, solid units, lyophilized, spray freeze dried, spray dried, and the like). The mixture is provided at a second end 812. The fluid (the diluent, gas or liquid) is introduced to the venturi system 800 at the first end 808 of mixing chamber 802. At the low pressure region (near the venturi throat 810), the diluent and bulk intermediate medicament is drawn into the stream of the fluid and reconstituted.

Once the bulk intermediate medicament is mixed, the resulting final medicament is withdrawn from the Venturi system 800. In example embodiments, the final medicament is withdrawn into a primary container disposed in the wearable injection device or to be inserted into the wearable injection device. In exemplary embodiments, the Venturi system 800 is provided separately from the wearable injection device. In alternative embodiments, the Venturi system 800 is provided within the wearable injection device. The Venturi system 800 may be reusable where the user is able to load the bulk intermediate medicament and diluent, or one or the other, into the Venturi system 800.

Figure 9A:
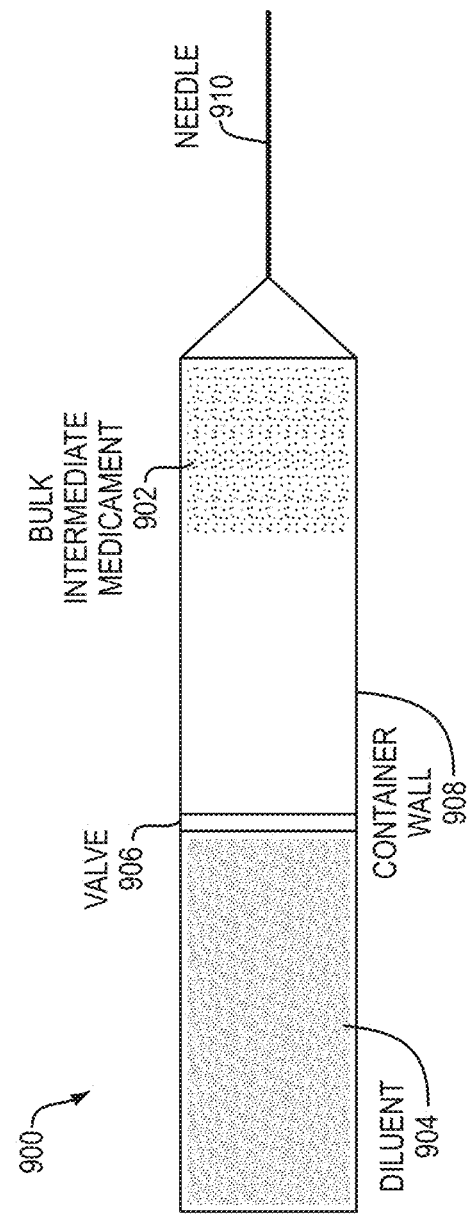
FIG. 9A illustrates a mixing mechanism using a valve in a container, according to an example embodiment.

FIG. 9A illustrates an exemplary embodiment of a container 900 including a valve 906 separating a diluent container and a bulk intermediate medicament container. In this embodiment, a bulk intermediate medicament 902, a diluent 904 and a valve 906 are disposed in a container 900 having a container wall 908. The container 900 may be coupled to a needle 910. The bulk intermediate medicament 902 may be disposed at a first end of the container 900, while the diluent 904 is disposed at a second end (opposing the first end) of the container 900. The valve 906 may be disposed between the bulk intermediate medicament 902 and the diluent 904 forming two containers or chambers within the container 900. The valve 906 is any controllable mechanism of separating one chamber from another.

The bulk intermediate medicament 902 may be applied to the container so that a layer of bulk intermediate medicament 902 is disposed on or coupled to an inner surface of the container wall 908, in some embodiments, using an adhesive that does not interfere with the bulk intermediate medicament 902. The bulk intermediate medicament 902 may be applied to the inner surface of the container wall 908 such that the bulk intermediate medicament 902 stays on the wall 908 during any transport of the container or injection device. Alternatively, the bulk intermediate medicament 902 may be freely disposed in the container at the proximal end. The bulk intermediate medicament 902 may be provided in dried form (powder, solid units, lyophilized, spray freeze dried, spray dried, and the like). The valve 906 may be disposed in the container 900 so that it fits snugly around the inner surface, thus, not allowing any diluent to pass to the chamber holding the bulk intermediate medicament 902.

When the valve 906 is activated upon activation of the activation mechanism 110 via actuation of button 165, and it causes an orifice in the valve to open. The diluent 904 flows from the distal end to the proximal end of the container 900 mixing with the bulk intermediate medicament 902. Actuation by a user of the exemplary activation mechanism 110 discussed above may trigger the valve 906 to initiate the mixing process. The bulk intermediate medicament 902 and diluent 904 may be prefilled in the container 900 by a manufacturer or pharmacy. Alternatively, the bulk intermediate medicament 902 and the diluent 904 may be loaded by the user, including the valve 906 in some embodiments. After the mixing process is complete, the mixture in the container 900 is ready for the injection process. The container 900 is fluidically coupled to the activation mechanism 110 and the injection assembly 120 (discussed above) in the housing 105 of the wearable injection device to inject the patient with the final medicament. The user may insert the container 900 into the wearable injection device, or the container is provided within the wearable injection device.

In some embodiments, the valve 906 is a rupturable membrane. At time of mixing, the membrane ruptures, allowing the diluent 904 to mix with the bulk intermediate medicament 902. In an example embodiment, instead of breaking completely, the membrane may develop one or more orifices therein, allowing for fluid communication between the bulk intermediate medicament 902 and the diluent. The mixture in the container 900 can be oscillated, manually or automatically, between the proximal end and distal end to allow for the bulk intermediate medicament 902 and the diluent 904 to mix thoroughly.

Figure 9B:
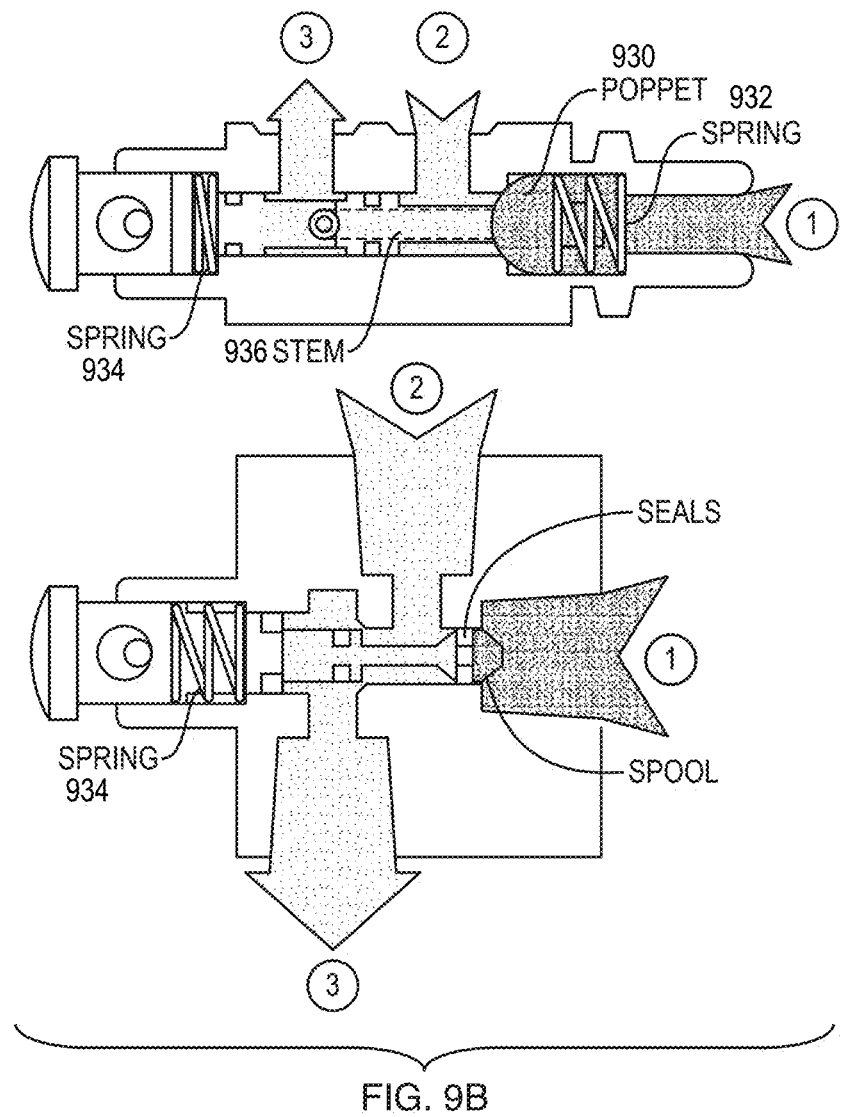
FIG. 9B illustrates a mixing mechanism using a valve in a container, according to an example embodiment.

In an example embodiment, the valve 906 may be a bistable mechanism, for example, an elastomeric valve that is sealed until a preset pressure difference is present, then the valve opens fully. In another example embodiment, the valve 906 may be a spring-loaded check or poppet valve, as shown in FIG. 9B, that remains sealed until a preset pressure difference is present. A poppet valve can be used to control the timing and quantity of liquid flow into a container. The poppet valve includes a hole, usually round or oval, and a tapered plug, usually a disk shape on the end of a shaft also called a valve stem. The portion of the hole where the plug meets with it is referred as the seat or valve seat. The value 906 shown in FIG. 9B includes a popper 930, a spring 932, a spring 943, and a stem 936.

Alternatively, the valve 906 may be a magnetically-actuated valve that allows for the diluent or the bulk intermediate medicament to flow through for mixing purposes, and that is activated when a magnet, external to the container, is moved relative to the valve 906. In yet another embodiment, the valve 906 may be an elastomeric pinch valve which is actuated by removing an external pinch force, for example, by moving or toggling a slider or button. The pinch force squeezes an internal lumen to occlude fluid flow. The slider or button may be provided on an outer surface of container 900 so a user can actuate the slider or button to operate the valve.

In other embodiments, the valve 906 may be a rotary valve that may be actuated by twisting the container or the housing of the wearable injection device. Alternatively, the valve 906 may be a spool valve actuated by axially translating the spool. In another example embodiment, the diluent may be contained in an ampule with a fracturable neck that can be fractured or broken by manipulation of the housing or the container, thus releasing the diluent into the mixing chamber or the intermediate container holding the bulk intermediate medicament.

Figure 9C:
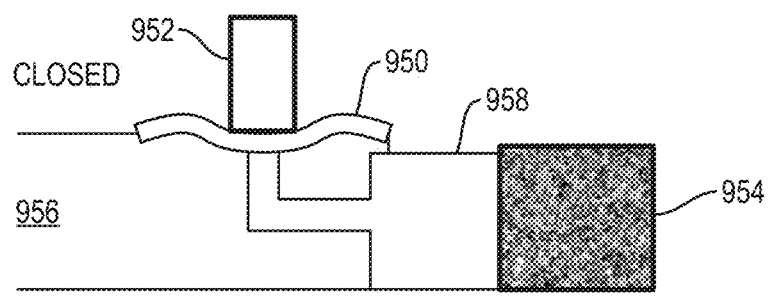
FIG. 9C illustrates a mixing mechanism using a valve in a container, according to an example embodiment.
Figure 9D:
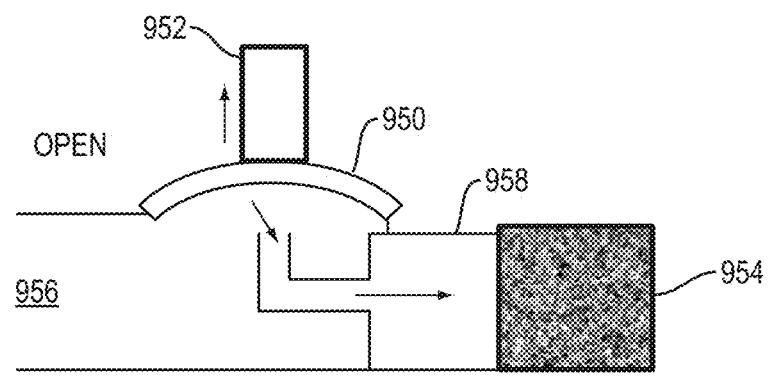
FIG. 9D illustrates a mixing mechanism using a valve in a container, according to an example embodiment.

In yet another example, as shown in FIG. 9C, the valve 906 may be an elastomeric seal 950 that is released by removal of an external retaining member such as a snap-on cap or top 952. The bulk intermediate medicament may be provided in container 954, and the diluent may be provided in chamber 956. The mixing of the bulk intermediate medicament and the diluent occurs in chamber 958 when the elastomeric seal 952 is released as shown in FIG. 9D. Alternatively, the elastomeric seal may also constitute a diaphragm-pump element such that once the cap is removed, pushing on the elastomeric element pumps the mixture back and forth to promote thorough mixing. Oscillation of the diaphragm may create oscillating flow in the mixture and promote mixing.

In this manner, this exemplary embodiment provides separate storage for the bulk intermediate medicament and diluent, and reconstitution means for the drug and the diluent. This exemplary embodiment can also be used to mix a bulk intermediate medicament and liquid, where complete reconstitution of the bulk intermediate medicament is not required.

Figure 10:
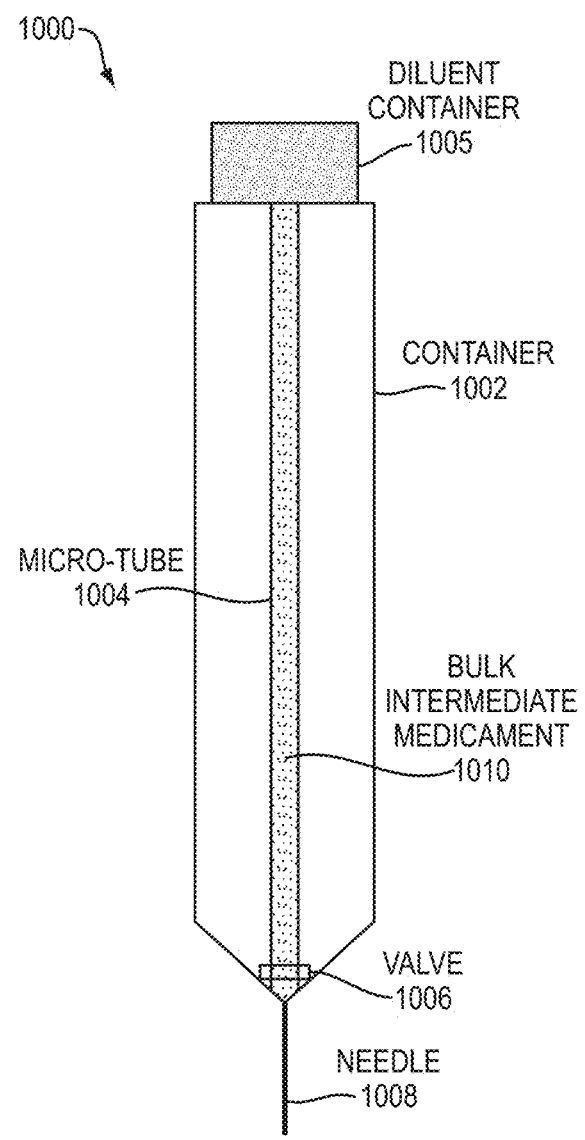
FIG. 10 illustrates a mixing mechanism using a microtube, according to an example embodiment.

FIG. 10 illustrates an exemplary embodiment of a mixing container 1000 having a micro-tube. The container 1000 includes a micro-tube 1004 longitudinally extending in an internal portion of the container 1000. In some embodiments, the micro-tube 1004 may have an internal diameter between 250 microns and 500 microns. In some embodiments, the micro-tube 1004 may have an internal diameter smaller than 1000 microns. The inner surface of the micro-tube 1004 is coated with a bulk intermediate medicament 1010 in dried form, such as a powder. The container 1000 is coupled to a diluent container 1005 holding a diluent. Upon activation of the activation mechanism 110, for example, via the button 165, the diluent flows through the micro-tube, such that a large surface area is provided for the diluent to dissolve the coated bulk intermediate medicament 1010. The diluent passes through the micro-tube 1004 dissolving the bulk intermediate medicament 1010 as it flows through the micro-tube 1004. The resulting mixture is collected or provided in the internal portion of the container 1000. The container 1000 may further include a vent or a valve 1006 to release/remove any trapped gas before injecting the medicament. First the gas is ejected by the valve or vent 1006, then the valve is closed, and then the mixture is injected.

After the mixing process is complete, the mixture in the container 1000 is ready for the injection process. The container is fluidically coupled to the activation mechanism 110 and the injection assembly 120 (discussed above) in the housing 105 of the wearable injection device to inject the patient with medicament.

Figure 11:
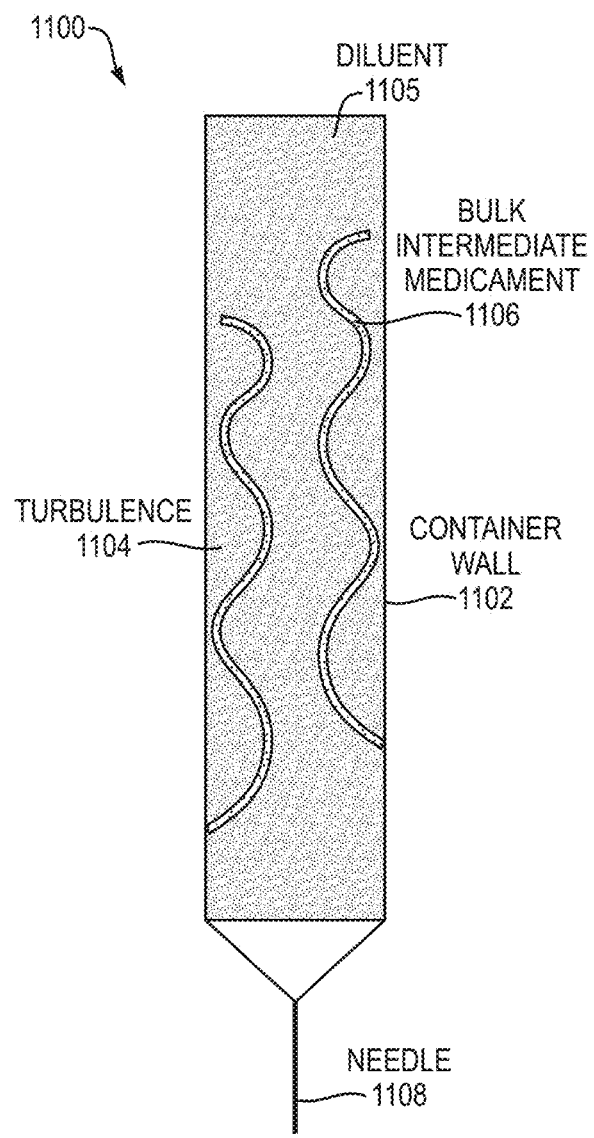
FIG. 11 illustrates a mixing mechanism using a turbulent surface, according to an example embodiment.

FIG. 11 illustrates an exemplary embodiment of a mixing container 1100 having a turbulent-producing surface 1104 to cause mixing of the bulk intermediate medicament 1106 and diluent 1105. The container 1100 includes a turbulent-producing surface 1104, and a bulk intermediate medicament 1106. The container 1100 may also be coupled to a needle 1108. The turbulent-producing surface 1104 may be disposed on an inner container wall 1102 as illustrated. The turbulent-producing surface 1104 may be provided as grooves, bumps, trenches, valleys, notches, or any combination thereof on the inner surface of container wall 1102.

A bulk intermediate medicament 1106 in dried form, such as a powder, may be applied to the surface of the turbulent-producing surface 1104. Upon activation of the activation mechanism 110, for example via the button 165, a diluent 1105 may be introduced into the container 1100. The flow of the diluent 1105 through the container 1100 causes the bulk intermediate medicament 1106 to release from the surface of the turbulent-producing surface 1104. Additionally, the turbulent-producing surface 1104 causes turbulence in the flow of the diluent 1105, in turn causing mixing of the bulk intermediate medicament and the diluent. In some embodiments, a user may agitate the container 1100 to cause mixing of the diluent and the bulk intermediate medicament to form a mixture. After the mixing process is complete, the mixture in the container is ready for the injection process. The container may be fluidically coupled to the activation mechanism 110 and the injection assembly 120 (discussed above) in the housing 105 of the wearable injection device to inject the patient with medicament. Alternatively, the mixture may be transferred to a primary container 130 in the housing 105 of the wearable injection device.

Figure 12:
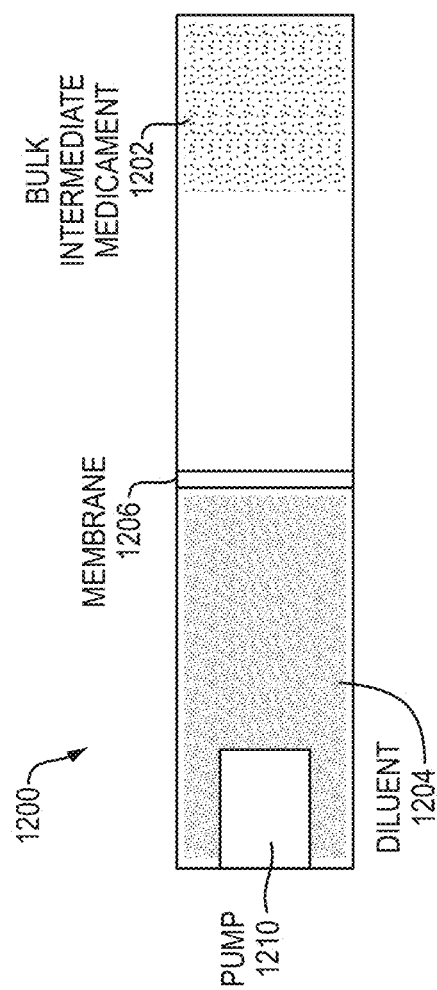
FIG. 12 illustrates a mixing mechanism using an ionic membrane, according to an example embodiment.

FIG. 12 illustrates an exemplary electrochemical mixing mechanism that includes movement of an ionic solution 1204 across a membrane 1206. An exemplary system may include an osmotic mini-pump 1210 where the container 1200 includes the bulk intermediate medicament 1202, the diluent 1204 in form of an ionic solution, and an osmotic membrane 1206. Upon activation of the activation mechanism 110, for example, via the button 165, the osmotic mini-pump is activated, and causes the ionic solution (diluent) 1204 to move across the osmotic membrane 1206 to the bulk intermediate medicament 1202 to allow for mixing to form a final medicament prior to injection.

Another exemplary mixing mechanism includes a plunger in a container, where the plunger stopper or piston has bypass channels that allow fluid to flow from a high pressure side of the piston to a low pressure side. The plunger may be moved back and forth within the container, as needed, to promote thorough mixing of the diluent and the bulk intermediate medicament.

In any of the above exemplary embodiments of mixing mechanisms or chambers, a user may initiate the mixing process by actuating a button (disposed on the wearable injection device or the mixing system) or by toggling or sliding a lever (on the wearable injection device or the mixing system), or by using a touch-screen interface for user input, or by using a wireless remote device that is in wireless communication with the wearable injection device or mixing unit via a RFID, Bluetooth, or any other near-field communication mechanisms. This user action may trigger the activation mechanism, which in turn may initiate the reconstitution process by allowing the diluent and bulk intermediate medicament to mix, and in some embodiments by causing agitation of the diluent and bulk intermediate medicament. Agitation may be performed by rocking the container containing the bulk intermediate medicament and the diluent, by vigorously shaking the container, by using high frequency sonic waves with or without inducing fluid cavitation, by rotating the container, and/or by any other suitable means.

In some of the above embodiments, the bulk intermediate medicament may be a solid unit, or a plurality of solid units. As used herein, the term "solid unit," refers to a composition which is suitable for pharmaceutical administration and comprises a medicament, such as a protein, e.g., an antibody or peptide, and a stabilizer, e.g., a sugar. The solid unit has a structural rigidity and resistance to changes in shape and/or volume. In a preferred embodiment, the solid unit is obtained by lyophilizing a pharmaceutical formulation of a medicament, e.g., a therapeutic protein. The solid unit may be any shape, e.g., geometric shape, including, but not limited to, a sphere, a cube, a pyramid, a hemisphere, a cylinder, a teardrop, and so forth, including irregularly shaped units. In one embodiment, the solid unit has a volume ranging from about 1 µl to about 20 µl. In one embodiment, the solid unit is not obtained using spray drying techniques, e.g., the solid unit is not a powder or granule.

As used herein, the phrase "a plurality of solid units" refers to a collection or population of solid units, wherein the collection comprises two or more solid units having a substantially uniform shape, e.g., sphere, and/or volume distribution. In one embodiment, the plurality of solid units is free-flowing. A plurality of solid units, as used herein, is not a powder (a dry, bulk solid composed of a large number of very fine particles that may flow freely when shaken or tilted).

As used herein, the term "geometrically uniform" refers to a plurality of lyophilized solid units having substantially uniform shape and size. In one embodiment, a plurality of solid units that are geometrically uniform are spheres and have substantially similar diameters and protein concentrations.

As used herein, the term "free-flowing" refers to the ability of the plurality of solid units to move in unbroken continuity, similar to a fluid (e.g., the individual solid units within a plurality of solid units do not significantly adhere or stick to one another), prior to reconstitution in a diluent.

The terms "freeze-drying" and "lyophilizing", used interchangeably herein, refer to a process in which a solution comprising a medicament, e.g., a therapeutic protein, (e.g., a peptide, a DVD-Ig protein, or an antibody, or antigen-binding fragment thereof), is frozen and subsequently vacuum sublimated.

The term "nucleation" refers to a physical process in which a change of state, e.g., liquid to solid, occurs in a substance around certain focal points, known as nuclei. "Controlled nucleation" refers to nucleation of a substance under conditions that provide for homogeneous nucleation of a population of substances undergoing a physical process in which a change of state occurs. For example, freezing a plurality of solid units using controlled nucleation results in a population of solid units that are substantially homogenous, e.g., have similar pore size within each solid unit. Controlled nucleation can be achieved by instantaneously freezing a solution.

Exemplary embodiments provide a system for the delivery of any agent, but most especially pharmaceutical drug products such as therapeutic proteins. The system incorporates a lyophilization process, enabling controlled nucleation, to produce uniform, free flowing solid units.

Under typical lyophilization methods, a liquid solution is placed into a final primary container prior to lyophilization, resulting in a lyophilized cake. While traditional lyophilization is performed in the container in which the lyo-cake will be stored and eventually reconstituted, some embodiments provide a lyophilization process which can be independent of the primary container. Indeed, the example embodiments provides stable solid units which can be manufactured, subsequently stored, and then further processed according to specific needs. The free flowing solid units are of uniform geometry, volume, and composition, and are capable of being stored and managed as a large bulk volume, or as a single dose in a primary drug container without impact to the lyophilization process parameters.

Exemplary embodiments are applicable to a broad range of antibody, protein-based, small molecule, or combinations of pharmaceutical products with minimal changes to critical process parameters. Some embodiments provide solid units that may be used both as oral and injectable dosage forms.

In one embodiment, the bulk intermediate medicament may be a drug product comprising a plurality of lyophilized, spherical solid units which are free-flowing and geometrically uniform, wherein the plurality of solid units comprises a therapeutic protein and a sugar. The solid units within the drug product may be produced using a controlled nucleation.

An advantage of the solid unit or the plurality of solid units is that they present the opportunity to combine distinct agents that have separate formulation stability needs and are otherwise incompatible as far as combining in a single formulation. In cases where a biopharmaceutical product is made from a combination of two or more active agents, e.g., two antibodies having distinct antigen specificity, the agents must be able to be co-formulated in order to be lyophilized collectively as one product. This can be a challenge given that a common formulation must be identified in which both agents are stable and still biologically active. Exemplary embodiments do not require a common formulation in order to provide a combination of medicaments in one dosage form. For example, a plurality of solid units comprising two distinct antibody populations, i.e. solid units comprising a first antibody having specific to antigen 1 and solid units comprising a second antibody having a specificity to antigen 2, may be combined as free flowing spherical solid units which may be combined upon reconstitution in water or a buffered solution such that the resulting liquid formulation is stable for a given period of time sufficient for administration of the reconstituted formulation to a subject in need. Thus, in an example process each active medicament can be lyophilized in its preferred formulation, and then combined as a plurality of solid units until reconstitution is warranted.

Certain example processes produce stable drug product examples for many active pharmaceutical substances, including stability at room temperature and/or accelerated storage conditions for a protein, including a peptide, a DVD-Ig protein, and an antibody, or antigen-binding portion thereof.

Thus, stable solid units (and pluralities thereof) can be provided, where the solid units contain a medicament, such as a protein (e.g., an antibody, or antigen-binding portion thereof), and a stabilizer, e.g., a sugar such as sorbitol, mannitol, sucrose or trehalose. Exemplary embodiments are directed to a stable solid unit suitable for pharmaceutical administration where the solid unit comprises a protein, such as, but not limited to a peptide, an antibody, or antigen-binding portion thereof, or a DVD-Ig protein, and a stabilizer, such as a lyoprotectant, e.g., a sugar.

The solid units provide many advantages due to their stability and the ability to make homogenous populations of solid units having similar sizes and agent (e.g., protein) content. The solid units, when considered together, are free flowing. Further, solid units may be geometrically uniform. The solid units are not produced using spray-drying or sprayfreeze drying techniques. Such techniques do not result in a population of solid units having consistent features, e.g., geometric uniformity, in contrast to the solid units described herein.

The solid units described herein are stable, in that they can maintain stability of a medicament, e.g., a protein, (e.g., antibody or antigen-binding portion thereof), over time, including at high temperatures. In one embodiment, a stable solid unit is provided suitable for pharmaceutical administration, said lyophilized solid unit comprising a mixture of an anti-human TNFα antibody, or an antigen-binding portion thereof, and a stabilizer, wherein the stabilizer prevents or reduces chemical or physical instability of the antibody, or antigen-binding portion thereof, upon freeze-drying and subsequent storage.

The solid unit may include a polymer within the solid unit and/or as a coating on the outside of the solid unit. Polymers that may be combined with the solid unit include, but are not limited to, a bioadhesive polymer, an enteric protectant, a non-pH sensitive polymer, and a sustained-release polymer (and combinations thereof).

In one embodiment, the solid unit is made under aseptic conditions.

A solid unit may have a volume ranging from about 0.0005 µl to about 20 µl, about 0.005 µl to about 20 µl, 0.001 µl to about 20 µl, 0.05 µl to about 20 µl, 0.01 µl to about 20 µl, 0.0005 µl to about 10 µl, about 0.005 µl to about 10 µl, 0.001 µl to about 10 µl, 0.05 µl to about 10 µl, 0.01 µl to about 10 µl, 0.0005 µl to about 5 µl, about 0.005 µl to about 5 µl, 0.001 µl to about 5 µl, 0.05 µl to about 5 µl, 0.01 µl to about 5 µl, 0.0005 µl to about 1 µl, about 0.005 µl to about 1 µl, 0.001 µl to about 1 µl, 0.05 µl to about 1 µl, 0.01 µl to about 1 µl, about 0.1 µl to about 20 µl, about 0.5 to about 20, about 1 to about 20, about 1.5 to about 20, about 2 to about 20, about 2.5 to about 20, about 3 to about 20, about 3.5 to about 20, about 4 to about 20, about 4.5 to about 20, about 5 to about 20, about 5.5 to about 20, about 6 to about 20, about 6.5 to about 20, about 7 to about 20, about 7.5 to about 20, about 8 to about 20, about 8.5 to about 20, about 9 to about 20, about 9.5 to about 20, about 10 to about 20, about 15 to about 20, about 12 to about 20, about 13 to about 20, about 14 to about 20, about 15 to about 20, about 16 to about 20, about 17 to about 20, about 18 to about 20, about 19 to about 20, about 0.5 to about 15, about 1 to about 15, 1.5 to about 15, about 2 to about 15, about 2.5 to about 15, about 3 to about 15, about 3.5 to about 15, about 4 to about 15, about 4.5 to about 15, about 5 to about 15, about 5.5 to about 15, about 6 to about 15, about 6.5 to about 15, about 7 to about 15, about 7.5 to about 15, about 8 to about 15, about 8.5 to about 15, about 9 to about 15, about 9.5 to about 15, or about 10 µl to about 15 µl. In one embodiment, the solid unit has a volume of between about 9 µl and 15 µl. Volumes and ranges intermediate to the above recited volumes and ranges are also intended to be part of exemplary embodiments (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 52.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or about 20.0 μl).

A solid unit may be any suitable shape. In one embodiment, the solid unit is a geometric shape, e.g., a sphere, a cube, a cylinder, or a pyramid. In one embodiment, a solid unit is a sphere having a diameter of about 0.1 to about 4 mm; about 0.1 to about 3.5 mm; about 0.1 to about 3 mm; about 0.1 to about 2.5 mm; about 0.1 to about 2 mm; about 0.1 to about 1.5 mm; about 0.1 to about 1 mm; or about 0.1 to about 0.5 mm. Diameters and ranges intermediate to the above recited diameters and ranges are also intended to be part of exemplary embodiments (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0 mm). Other exemplary ranges include about 0.1 to about 4 mm; about 0.1 to about 3 mm; about 0.1 to about 2 mm; about 0.1 to about 1 mm; and about 0.1 to about 0.5 mm.

In one embodiment, the solid units are spherical in shape. A solid unit that is spherical in shape has approximately the same diameter regardless of the point at which the calculation is taken on the outside of the solid unit. Thus, a sphere does not include a partial sphere, i.e., a sphere with a flat surface(s).

In one embodiment, the solid unit is a sphere having a diameter which is greater than 1 mm and less than 4 mm.

In one embodiment, the solid unit contains a protein, e.g., a peptide, a DVD-Ig protein, or an antibody or antigen-binding portion thereof, and an additional medicament.

Solid units are particularly useful in providing a consistent means for measuring a dose of a medicament, such as a therapeutic agent, such as a protein (e.g., an antibody, antigen-binding portion thereof, or a DVD-Ig protein). As a plurality of the solid units may have substantially the same shape, the solid units in turn have substantially similar amounts of medicament, e.g., protein. Thus, the amount of agent, such as a protein, (e.g., antibody, or antigen-binding portion thereof), in a solid unit, (such as a sphere shaped solid unit), may be between about 0.02 μg and 6.0 mg, about 0.05 μg to about 6.0 mg, about 0.1 μg to about 6.0 mg, about 0.2 μg to about 6.0 mg, about 0.5 μg to about 6.0 mg, about 1 μg to about 6.0 mg, about 5 μg to about 6.0 mg, about 10 μg to about 6.0 mg, about 15 μg to about 6.0 mg, 0.02 μg and 4.0 mg, about 0.05 μg to about 4.0 mg, about 0.1 μg to about 4.0 mg, about 0.2 μg to about 4.0 mg, about 0.5 μg to about 4.0 mg, about 1 μg to about 4.0 mg, about 5 μg to about 4.0 mg, about 10 μg to about 4.0 mg, about 15 μg to about 4.0 mg, 0.02 μg and 2.0 mg, about 0.05 μg to about 2.0 mg, about 0.1 μg to about 2.0 mg, about 0.2 μg to about 2.0 mg, about 0.5 μg to about 2.0 mg, about 1 μg to about 2.0 mg, about 5 μg to about 2.0 mg, about 10 μg to about 2.0 mg, about 15 μg to about 2.0 mg, about 0.02 μg and 1.0 mg, about 0.05 μg to about 1.0 mg, about 0.02 μg and 1.0 mg, about 0.05 μg to about 1.0 mg, about 0.1 μg to about 1.0 mg, about 0.2 μg to about 1.0 mg, about 0.5 μg to about 1.0 mg, about 1 μg to about 1.0 mg, about 5 μg to about 1.0 mg, about 10 μg to about 1.0 mg, about 15 μg to about 1.0 mg, about 0.02 μg and 0.5 mg, about 0.05 μg to about 0.5 mg, about 0.1 μg to about 0.5 mg, about 0.2 μg to about 0.5 mg, about 0.5 μg to about 0.5 mg, about 1 μg to about 0.5 mg, about 5 μg to about 0.5 mg, about 10 μg to about 0.5 mg, about 15 μg to about 0.5 mg, about 0.02 μg and 0.25 mg, about 0.05 μg to about 0.25 mg, about 0.1 μg to about 0.25 mg, about 0.2 μg to about 0.25 mg, about 0.5 μg to about 0.25 mg, about 1 μg to about 0.52 mg, about 5 μg to about 0.25 mg, about 10 μg to about 0.25 mg, about 15 μg to about 0.25 mg, about 0.02 μg and 0.1 mg, about 0.05 μg to about 0.1 mg, about 0.1 μg to about 0.1 mg, about 0.2 μg to about 0.1 mg, about 0.5 μg to about 0.1 mg, about 1 μg to about 0.1 mg, about 5 μg to about 0.1 mg, about 10 μg to about 0.1 mg, about 15 μg to about 0.1 mg, about 0.02 μg and 0.05 mg, about 0.05 μg to about 0.05 mg, about 0.1 μg to about 0.05 mg, about 0.2 μg to about 0.05 mg, about 0.5 μg to about 0.05 mg, about 1 μg to about 0.05 mg, about 5 μg to about 0.05 mg, about 10 μg to about 0.05 mg, or about 15 μg to about 0.05 mg. Amounts and ranges intermediate to the above recited amounts and ranges are also intended to be part of exemplary embodiments. Other exemplary ranges of agent, e.g., protein, amount include 0.02 μg to 6.0 mg or 15 μg to 4.0 mg of therapeutic protein.

In certain embodiments, the amount of medicament, such as a protein (e.g., an antibody, or antigen-binding portion thereof, peptide, or DVD-Ig protein) in a solid unit, such as a sphere shaped solid unit, may be between about 0.02 μg and 2.0 mg and the diameter of the sphere may be between about 0.1 mm to about 4 mm. In other embodiments, the amount of medicament, such as a protein (e.g., an antibody, or antigen-binding portion thereof, peptide, or a DVD-Ig protein) in a solid unit, such as a sphere shaped solid unit, may be between about 0.02 μg and 1.5 mg and the diameter of the sphere may be between about 0.1 mm to about 3 mm. In yet other embodiments, the amount of medicament, such as a protein (e.g., an antibody, or antigen-binding portion thereof, peptide, or a DVD-Ig protein) in a solid unit, such as a sphere shaped solid unit, may be between about 0.02 μg and 500 μg and the diameter of the sphere may be between about 0.1 mm to about 2 mm. In some embodiments, the amount of medicament, such as a protein (e.g., an antibody, or antigen-binding portion thereof, peptide, or a DVD-Ig protein) in a solid unit, such as a sphere shaped solid unit, may be between about 0.02 μg and 50 μg and the diameter of the sphere may be between about 0.1 mm to about 1 mm. In other embodiments, the amount of medicament, such as a protein (e.g., an antibody, or antigen-binding portion thereof, peptide, or a DVD-Ig protein) in a solid unit, such as a sphere shaped solid unit, may be between about 0.02 μg and 6 μg and the diameter of the sphere may be between about 0.1 mm to about 0.5 mm. Amounts, diameters and ranges intermediate to the above recited amounts, diameters and ranges are also intended to be part of exemplary embodiments.

In one embodiment, the solid unit contains a medicament, such as a protein (e.g., an antibody, or an antigen-binding portion thereof, peptide, or a DVD-Ig protein) and sorbitol, sucrose or trehalose, where the amount of sorbitol, sucrose or trehalose is sufficient to maintain the stability of the medicament, such as a protein (e.g., peptide, DVD-Ig protein, or antibody, or antigen-binding portion thereof), for at least 12 months of storage at about 25° C. storage. Alternatively, the amount of sorbitol, sucrose or trehalose in the solid unit is sufficient to maintain stability of the medicament, such as a protein (e.g., an antibody, or antigen-binding portion thereof, peptide, or DVD-Ig protein) for at least 3 months of storage at about 40° C.

In one embodiment, the solid unit contains a medicament, such as a protein (e.g., an antibody, or an antigen-binding portion thereof, peptide, or a DVD-Ig protein) and mannitol, where the amount of mannitol is sufficient to maintain the stability of the agent, such as a protein (e.g., an antibody, or an antigen-binding portion thereof, peptide, or a DVD-Ig protein), for at least 12 months of storage at about 25° C. Alternatively, the amount of mannitol in the solid unit is sufficient to maintain stability of the agent, such as a protein (e.g., an antibody, or an antigen-binding portion thereof, peptide, or a DVD-Ig protein), or for at least 3 months of storage at about 40° C.

Stability of the medicament, such as a protein (e.g., an antibody, or antigen-binding portion thereof, peptide, or DVD-Ig protein) may be determined according to any method known in the art, including those described in the Examples herein. Size exclusion chromatography (SEC) may be used to determine fragment and monomer (aggregation) content for protein, such as antibodies, within a solid unit. In one embodiment, stability of the medicament, such as a protein (e.g., an antibody, peptide, or DVD-Ig protein) is determined by dissolving the solid unit containing the medicament, such as a protein (e.g., an antibody or antigen-binding portion thereof, peptide, or DVD-Ig protein), in water following storage (e.g., 12 months of storage at about 25° C. storage or 3 months of storage at about 40° C.) and performing SEC. In one embodiment, storage of the solid unit is performed at 25° C. under 55-65% relative humidity in a closed container. Alternatively, storage of the solid unit may be performed at 40° C. under 70-80% relative humidity in a closed container.

In one embodiment, SEC results indicating 90% or more monomer antibody, or antigen-binding portion thereof, indicates stability of the solid unit and antibody or antigen-binding portion thereof, contained therein. In one embodiment, SEC results indicating 95% or more monomer antibody, or antigen-binding portion thereof, indicates stability of the solid unit and antibody or antigen-binding portion thereof, contained therein. In one embodiment, SEC results indicating 96% or more monomer antibody, or antigen-binding portion thereof, indicates stability of the solid unit and antibody or antigen-binding portion thereof, contained therein. In one embodiment, SEC results indicating 97% or more monomer antibody, or antigen-binding portion thereof, indicates stability of the solid unit and antibody or antigen-binding portion thereof, contained therein. In one embodiment, SEC results indicating 98% or more monomer antibody, or antigen-binding portion thereof, indicates stability of the solid unit and antibody or antigen-binding portion thereof, contained therein. In one embodiment, SEC results indicating 99% or more monomer antibody, or antigen-binding portion thereof, indicates stability of the solid unit and antibody or antigen-binding portion thereof, contained therein. In one embodiment, SEC results indicating 99.5% or more monomer antibody, or antigen-binding portion thereof, indicates stability of the solid unit and antibody or antigen-binding portion thereof, contained therein. The monomer percentages described above also relate to solid units comprising DVD-Ig proteins.

Monomer percentages may also be described in terms of percent (%) aggregate. For example, in one embodiment, a plurality of solid units is provided having less than 30% aggregate protein (e.g., peptide, antibody or DVD-Ig protein) as determined by SEC, less than 25% aggregate protein (e.g., peptide, antibody or DVD-Ig protein) as determined by SEC, less than 20% aggregate protein (e.g., peptide, antibody or DVD-Ig protein) as determined by SEC, less than 15% aggregate protein (e.g., peptide, antibody or DVD-Ig protein) as determined by SEC, less than 10% aggregate protein (e.g., peptide, antibody or DVD-Ig protein) as determined by SEC, less than 5% aggregate protein (e.g., peptide, antibody or DVD-Ig protein) as determined by SEC, less than 4% aggregate protein (e.g., peptide, antibody or DVD-Ig protein) as determined by SEC, less than 3% aggregate protein (e.g., peptide, antibody or DVD-Ig protein) as determined by SEC, less than 2% aggregate protein (e.g., peptide, antibody or DVD-Ig protein) as determined by SEC, less than 1% aggregate protein (e.g., peptide, antibody or DVD-Ig protein) as determined by SEC.

A solid unit may have a stabilizer:protein ratio ranging from about 0.8 to about 3.5:1.0 w/w, from about 0.8 to about 3.0:1.0 w/w, from about 0.8 to about 2.5:1.0 w/w, from about 0.8 to about 2.0:1.0 w/w, from about 0.8 to about 1.5:1.0 w/w, from about 0.9 to about 2.0:1 w/w, from about 0.9 to about 1.5:1.0 w/w, from about 0.1 to 3.5:1 w/w, from about 0.1 to 10:1 w/w, or from about 1.0:1.0 w/w. Examples of proteins having these exemplary stabilizer:protein ratios include, but are not limited to, peptide, antibodies, and DVD-Ig proteins. Values and ratios intermediate to the above recited values and ratios are also intended to be part of exemplary embodiments.

In one embodiment, the ranges of molar ratios of stabilizer (sugar):antibody are 284:1 to 638:1. Alternatively, the range of molar ratio of stabilizer (sugar):antibody is 511:1 to 638:1; 520:1 to 638:1; 530:1 to 638:1, and so forth.

A stable solid unit may also be suitable for pharmaceutical administration, comprising protein e.g., a peptide, DVD-Ig protein, or an antibody, or antigen-binding portion thereof, and sucrose, wherein the sucrose:peptide, DVD-Ig protein, or antibody, or antigen-binding portion thereof, ratio ranges from about 0.8 to 3.5:1 weight/weight (w/w), from about 0.8 to about 3.0:1.0 w/w, from about 0.8 to about 2.5:1.0 w/w, from about 0.8 to about 2.0:1.0 w/w, from about 0.8 to about 1.5:1.0 w/w, from about 0.9 to about 2.0:1 w/w, from about 0.9 to about 1.5:1.0 w/w, from about 0.1 to 3.5:1 w/w, from about 0.1 to 10:1 w/w; or from about 1.0:1.0 w/w. Values and ratios intermediate to the above recited values and ratios are also intended to be part of exemplary embodiments.

A stable solid unit may also be suitable for pharmaceutical administration, comprising a protein (e.g., a peptide, DVD-Ig protein, or an antibody, or antigen-binding portion thereof), and sorbitol, wherein the sorbitol:peptide, DVD-Ig protein, or antibody, or antigen-binding portion thereof, ratio ranges from about 0.8 to 3.5:1 weight/weight (w/w), from about 0.8 to about 3.0:1.0 w/w, from about 0.8 to about 2.5:1.0 w/w, from about 0.8 to about 2.0:1.0 w/w, from about 0.8 to about 1.5:1.0 w/w, from about 0.9 to about 2.0:1 w/w, from about 0.9 to about 1.5:1.0 w/w, from about 0.1 to 3.5:1 w/w, from about 0.1 to 10:1 w/w, or from about 1.0:1.0 w/w. Values and ratios intermediate to the above recited values and ratios are also intended to be part of exemplary embodiments.

A stable solid unit suitable for pharmaceutical administration, comprising a protein, (e.g., a peptide, a DVD-Ig protein, or an antibody, or antigen-binding portion thereof(, and trehalose, wherein the trehalose:peptide, DVD-Ig protein, or antibody, or antigen-binding portion thereof, ratio ranges from about 0.8 to 3.5:1 weight/weight (w/w), from about 0.8 to about 3.0:1.0 w/w, from about 0.8 to about 2.5:1.0 w/w, from about 0.8 to about 2.0:1.0 w/w, from about 0.8 to about 1.5:1.0 w/w, from about 0.9 to about 2.0:1 w/w, from about 0.9 to about 1.5:1.0 w/w, from about 0.1 to 3.5:1 w/w, from about 0.1 to 10:1 w/w, or from about 1.0:1.0 w/w. Values and ratios intermediate to the above recited values and ratios are also intended to be part of exemplary embodiments.

In one embodiment, the concentration of sucrose in a solution for preparation of the solid unit is selected from the group consisting of about 10 mg/ml, about 20 mg/ml, about 30 mg/ml to about 100 mg/ml; about 40 mg/ml to about 90 mg/ml; about 40 mg/ml to about 80 mg/ml; about 40 mg/ml to about 70 mg/ml; about 40 mg/ml to about 60 mg/ml; and about 40 mg/ml to about 50 mg/ml. In one embodiment, the concentration of sucrose in a solution for preparation of the solid unit is about 10 mg/ml to about 200 mg/ml.

In one embodiment, the solid unit(s) are prepared from a solution comprising about 10 to about 40 mg/mL of mannitol and about 60 mg/mL to about 80 mg/mL of sucrose.

In one embodiment, the solid unit comprises a surfactant, e.g., a polysorbate.

In one embodiment, the solid unit does not include specific agents known to be traditional carriers for protein formulations. For example, in one embodiment, the solid unit does not comprise albumin, e.g., bovine serum albumin (BSA), or milk. Both albumin and milk, for example, are carriers used traditionally in protein formulations but are preferably excluded from the solid units, including solid units comprising a therapeutic protein (such as a peptide, DVD-Ig protein, or an antibody, or antigen-binding portion thereof).

In one embodiment, the solid unit does not comprise tromethamine. Thus, included in exemplary embodiments is a solid unit (or plurality of solid units) comprising a medicament, such as a therapeutic protein, (e.g., a peptide, DVD-Ig protein, or an antibody, or antigen-binding portion thereof), and excluding tromethamine. In a further embodiment, the solid unit described herein (or the plurality thereof) does not contain casein. In a further embodiment, the solid unit described herein (or the plurality thereof) does not contain a preservative, such as sodium azide. Such solid units may also be free flowing and have geometric uniformity.

In one embodiment, the solid unit contains more than one type of protein, e.g., two antibodies that bind distinct epitopes.

The solid units are further stable in that they are free-flowing and are able to be stored in humid conditions despite containing sugars. For example, the solid units, in one embodiment, have a low moisture content, e.g., 2% or less moisture, 1% or less moisture, 0.9% or less moisture, 0.8% or less moisture, 0.7% or less moisture, 0.6% or less moisture, 0.5% or less moisture, 0.4% or less moisture, 0.3% or less moisture, 0.1% to 3% moisture, 0.1% to 2% moisture, or 1% to 2% moisture, even in humid conditions, e.g., 60% or more humidity.

In one embodiment, the protein population within a solid unit comprising a therapeutic protein (e.g., a peptide, antibody, or DVD-Ig protein) is at least 90% the therapeutic protein, at least 95% the therapeutic protein, at least 96% the therapeutic protein, at least 97% the therapeutic protein, at least 98% the therapeutic protein, or at least 99% the therapeutic protein.

In certain embodiments, a solid unit encompasses post-translationally modified proteins, such as an antibody, or antigen-binding fragment thereof, as disclosed herein. For example, during post-translational processing, proteins are modified (e.g., chemical modification and folding) to produce a mature product (see, e.g., Berkowitz et al., *Nat Rev Drug Discov.* 11(7): 527-40, 2012, and references cited therein). Generally, modification is achieved by one or more events characterized broadly as the addition of biochemical functional groups (e.g., acetate, phosphate, lipids, and carbohydrates), modification of the chemical nature of an amino acid (e.g., citrullination), or structural modifications (e.g., formation of disulphide bridges). One of the most common post-translational modification to proteins involves glycosylation, which include, e.g., galactosylation, fucosylation, high mannose derivatives, and sialylation, e.g., N-linked or O-linked carbohydrate chains, processing of N-terminal or C-terminal ends. Additional post-translational modifications encompassed in some embodiments include, for example, oxidation, phosphorylation, sulphation, lipidation, disulphide bond formation, and deamidation, conversion of an N-terminal glutamate to pyroglutamate, deletion of a C-terminal amino acid, e.g., a C-terminal lysine), attachment of chemical moieties to the amino acid backbone, addition or deletion of an N-terminal methionine residue as a result of prokaryotic host cell expression. The proteins may also be modified with a detectable label, such as an enzymatic, fluorescent, isotopic or affinity label to allow for detection and isolation of the protein.

In one embodiment, solid units can be characterized according to the Table below, which describes the expected amount of protein given a spherical solid unit produced from a solution having either a 50 mg/ml protein concentration or 100 mg/ml protein. Thus, in one embodiment, the solid unit is a spherical solid unit having a diameter ranging from 0.1 mm to 3 mm, having a protein content of 0.00005 mg to 0.71 mg, and having a volume of 0.0005 microliters to 14.14 microliters.

Characterization of Protein Solid Units

| Diameter mm | Volume microliter | Area mm(2) | Protein mg mg (100) | Protein mg mg (50) | Protein mg mg (25) |
|---|---|---|---|---|---|
| 0.1 | 0.000524 | 0.031416 | 0.00005236 | 0.00002618 | 0.00001309 |
| 0.2 | 0.004189 | 0.125664 | 0.00041888 | 0.00020944 | 0.00010472 |
| 0.5 | 0.065 | 0.785 | 0.0065 | 0.0033 | 0.00164 |
| 0.8 | 0.268 | 2.011 | 0.0268 | 0.0134 | 0.00670 |
| 1 | 0.524 | 3.142 | 0.0524 | 0.0262 | 0.01309 |
| 1.5 | 1.767 | 7.069 | 0.1767 | 0.0884 | 0.04418 |
| 2 | 4.189 | 12.566 | 0.4189 | 0.2094 | 0.10472 |
| 2.5 | 8.181 | 19.635 | 0.8181 | 0.4091 | 0.20453 |
| 3 | 14.137 | 28.274 | 1.4137 | 0.7069 | 0.35343 |
| 3.5 | 22.449 | 38.485 | 2.2449 | 1.1225 | 0.56123 |
| 4 | 33.510 | 50.266 | 3.3510 | 1.6755 | 0.83776 |

In one embodiment, a lyophilized solid unit includes an antibody, or antigen-binding portion thereof, and an amount of sorbitol, sucrose or trehalose which prevents or reduces chemical or physical instability of the antibody, or antigen-binding portion thereof, upon lyophilizing and subsequent storage.

In one embodiment, a lyophilized solid unit of an antibody, or antigen-binding portion thereof, and an amount of sorbitol, sucrose or trehalose which prevents or reduces chemical or physical instability of the antibody, or antigen-binding portion thereof, upon lyophilizing and subsequent storage is included.

It should be noted that whenever a value or range of values of a parameter are recited, it is intended that values and ranges intermediate to the recited values are also intended to be part of exemplary embodiments.

In one embodiment, the solid units comprise an anti-human Tumor Necrosis Factor alpha (hTNFα) antibody, or antigen-binding portion thereof, comprising a light chain variable region comprising a CDR3 domain comprising an amino acid sequence set forth as SEQ ID NO: 3, a CDR2 domain comprising an amino acid sequence set forth as SEQ ID NO: 5, and a CDR1 domain comprising an amino acid sequence set forth as SEQ ID NO: 7, and a heavy chain variable region comprising a CDR3 domain comprising an amino acid sequence set forth as SEQ ID NO: 4, a CDR2 domain comprising an amino acid sequence set forth as SEQ ID NO: 6, and a CDR1 domain comprising an amino acid sequence set forth as SEQ ID NO: 8.

In one embodiment, the solid units comprise an anti-human Tumor Necrosis Factor alpha (hTNFα) antibody, or antigen-binding portion thereof, comprising a light chain variable region comprising the amino acid sequence set forth as SEQ ID NO: 1, and a heavy chain variable region of the antibody, or antigen-binding portion thereof comprising the amino acid sequence set forth as SEQ ID NO: 2.

In one embodiment, the solid units comprise an anti-human Tumor Necrosis Factor alpha (hTNFα) antibody, or antigen-binding portion thereof, comprising a light chain comprising the amino acid sequence set forth as SEQ ID NO: 9 and a heavy chain comprising the amino acid sequence set forth as SEQ ID NO: 10. In one embodiment, the acidic species of the antibody, or antigen-binding portion thereof, comprises AR1, AR2, or both AR1 and AR2.

In another embodiment, the solid unit comprises adalimumab, (or an antigen binding portion thereof), or a biosimilar thereof.

In one embodiment, the solid units comprise less than 15% of acidic species of the antibody, or antigen-binding portion thereof. In one embodiment, the acidic species of the antibody, or antigen-binding portion thereof, comprises AR1, AR2, or both AR1 and AR2. Alternatively, or in combination, the solid unit comprises about 70% lysine variant species of the antibody, or antigen-binding portion thereof, that have two C-terminal lysines (Lys 2) of the antibody, or antigen-binding portion thereof.

Notably, while medicaments are described herein, it is also a feature of the an example embodiment that the systems described herein could be used for any agent, including small molecules. Further, the systems described herein may be used for non-therapeutic use, e.g., in vitro analysis.

Some exemplary embodiments may use a plurality of solid units described herein. A plurality of solid units may, in some embodiments, have a substantially uniform size distribution and/or a volume distribution. In some instances, the plurality of solid units comprises populations of solid units having substantially uniform size distribution and/or a volume distribution. Notably, the plurality of solid units are not a powder (a power being a dry, bulk solid composed of a large number of very fine particles that may flow freely when shaken or tilted). Indeed, the plurality of the solid units described herein provide advantages over powders in that they provide consistency, for example in the size and uniformity of the plurality of solid units.

In one embodiment, a substantially uniform size distribution is intended to mean that the individual shapes and/or volumes of the solid units are substantially similar and not greater than a 20% standard deviation in volume. For example, a plurality of solid units which are spherical in shape would include a collection of solid units having no greater than 20% standard deviation from an average volume of the spheres. Alternatively, a substantially uniform size distribution indicates that the individual volumes of the solid units in a population are substantially similar and not greater than a 20% relative standard deviation in volume. Alternatively, a substantially uniform size distribution indicates that the individual volumes of the solid units in a population are substantially similar and not greater than a 15% standard deviation (or relative standard deviation) in volume; not greater than a 10% standard deviation (or relative standard deviation) in volume; or not greater than a 5% standard deviation (or relative standard deviation) in volume.

In one embodiment, each of the individual units within the plurality of units may have a substantially uniform volume, ranging from about 0.0005 µl to about 20 µl, about 0.005 µl to about 20 µl, 0.001 µl to about 20 µl, 0.05 µl to about 20 µl, 0.01 µl to about 20 µl, 0.0005 µl to about 10 µl, about 0.005 µl to about 10 µl, 0.001 µl to about 10 µl, 0.05 µl to about 10 µl, 0.01 µl to about 10 µl, 0.0005 µl to about 5 µl, about 0.005 µl to about 5 µl, 0.001 µl to about 5 µl, 0.05 µl to about 5 µl, 0.01 µl to about 5 µl, 0.0005 µl to about 1 µl, about 0.005 µl to about 1 µl, 0.001 µl to about 1 µl, 0.05 µl to about 1 µl, 0.01 µl to about 1 µl, 0.1 µl to about 20 µl, from about 0.5 µl to about 10 µl, about 0.5 to about 20, about 1 to about 20, about 1.5 to about 20, about 2 to about 20, about 2.5 to about 20, about 3 to about 20, about 3.5 to about 20, about 4 to about 20, about 4.5 to about 20, about 5 to about 20, about 5.5 to about 20, about 6 to about 20, about 6.5 to about 20, about 7 to about 20, about 7.5 to about 20, about 8 to about 20, about 8.5 to about 20, about 9 to about 20, about 9.5 to about 20, about 10 to about 20, about 15 to about 20, about 12 to about 20, about 13 to about 20, about 14 to about 20, about 15 to about 20, about 16 to about 20, about 17 to about 20, about 18 to about 20, about 19 to about 20, about 0.5 to about 15, about 1 to about 15, 1.5 to about 15, about 2 to about 15, about 2.5 to about 15, about 3 to about 15, about 3.5 to about 15, about 4 to about 15, about 4.5 to about 15, about 5 to about 15, about 5.5 to about 15, about 6 to about 15, about 6.5 to about 15, about 7 to about 15, about 7.5 to about 15, about 8 to about 15, about 8.5 to about 15, about 9 to about 15, about 9.5 to about 15, or about 10 µl to about 14 µl. In addition, a plurality of solid units may be substantially all spheres and have a volume ranging from any of the aforementioned volumes, including 0.0005 µl to about 20 µl, about 0.005 µl to about 20 µl, 0.001 µl to about 20 µl, 0.05 µl to about 20 µl, 0.01 µl to about 20 µl, 0.0005 µl to about 10 µl, about 0.005 µl to about 10 µl, 0.001 µl to about 10 µl, 0.05 µl to about 10 µl, 0.01 µl to about 10 µl, 0.0005 µl to about 5 µl, about 0.005 µl to about 5 µl, 0.001 µl to about 5 µl, 0.05 µl to about 5 µl, 0.01 µl to about 5 µl, 0.0005 µl to about 1 µl, about 0.005 µl to about 1 µl, 0.001 µl to about 1 µl, 0.05 µl to about 1 µl, 0.01 µl to about 1 µl, about 0.1 µl to about 20 µl or from about 0.5 µl to about 10 µl. Volumes and ranges intermediate to the above recited volumes and ranges are also intended to be part of exemplary embodiments (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0, 2.1, 2.2, 2.3, 2.4, 2.5, 2.6, 2.7, 2.8, 2.9, 3.0 µl). For spherical solid units, volume is related to diameter. For example, a spherical solid unit having a volume of about 0.05 µl has a diameter of about 0.2 mm, and a spherical solid unit having a volume of about 0.0005 µl has a diameter of about 0.1 mm.

In one embodiment, each of the solid units within the plurality of units may be substantially all spheres and have a diameter of about 0.1 to about 4 mm; about 0.1 to about 3 mm; about 0.1 to about 2 mm; about 0.1 to about 1 mm; or about 0.1 to about 0.5 mm. Diameters and ranges intermediate to the above recited diameters and ranges are also intended to be part of exemplary embodiments (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0 mm).

In a one embodiment, the plurality of subunits is suitable for pharmaceutical administration. The plurality of subunits may be manufactured under aseptic conditions.

One benefit of the plurality of solid units is that they remain free-flowing at room temperature and humidity, e.g., for at least 12 months at about 25° C. In one embodiment, the plurality of subunits is made of solid units having low moisture content, e.g., 1% or less moisture, 0.9% or less moisture, 0.8% or less moisture, 0.7% or less moisture, 0.6% or less moisture, 0.5% or less moisture, 0.4% or less moisture. Under certain conditions, e.g., under sealed containers, the solid units are able to maintain the low moisture content even in humid conditions, e.g., 60% or more humidity.

In some embodiments, a plurality of solid units are encapsulated within a shell or capsule, allowing them to, for example, be taken orally or be used as suppositories. Suitable capsules may be hard-shelled capsules or soft-shelled capsules, single-piece capsules or two-piece capsules. The solid units may also be pressed into a tablet which, in one embodiment, may be coated with an enteric coating.

An important feature of the plurality of solid units is that the plurality may, in certain embodiments, include two or more populations of solid units. For example, a plurality of solid units of exemplary embodiments may include populations of different therapeutic proteins, solid units having different sizes, solid units having different enteric protectants or enteric coatings allowing for release at different points of the GI tract, etc. The plurality of solid units may include solid units containing antibodies, or antigen binding portions thereof, directed to at least two distinct molecular targets. Thus, the plurality of solid units allows for combinations of solid units, e.g., solid units within the plurality containing different antibodies.

In one embodiment, a pharmaceutical composition is provided comprising a plurality of solid units composed of at least two different populations of solid units. The populations may be distinct based on any parameter, e.g., size, amount of medicament, the type of medicament, or any combinations thereof. Notably, the solid units are stable and remain free flowing even when combined in heterogeneous populations.

In one embodiment, a plurality of solid units is provided having at least two populations of solid units specific to different molecular targets, e.g., a peptide and/or an antibody, or antigen binding portion thereof, that bind at least two distinct molecular targets. The term "distinct molecular target" indicates that within a population two or more binding proteins are specific for distinct molecules, e.g., TNF and EGFR, or alternatively, are specific for specific epitopes within one molecule, e.g., epitopes one and two on TNF. Thus, the plurality of solid units of exemplary embodiments may include two or more populations of solid units comprising one population of solid units having a first peptide or first antibody, or an antigen binding portion thereof, and a second population of solid units having a second peptide or a second antibody, or antigen binding portion thereof, wherein the second peptide or second antibody, or antigen-binding portion thereof, is directed to a different molecular target or epitope than the first peptide or the first antibody, or antigen-binding portion thereof In one embodiment, a plurality of solid units is provided having at least two populations of solid units having substantially similar volumes and a second population of solid units having substantially similar volumes, wherein the first population and the second population have different volumes.

In one embodiment, a plurality of solid units is provided having two or more populations of solid units comprising one population of solid units having a first peptide or antibody, or a first antigen binding portion thereof, and a second population of solid units comprising an additional medicament.

In one embodiment, the two populations of solid units within the plurality make up at least about 70% of the plurality; at least about 80% of the plurality; at least about 90% of the plurality; at least about 95% of the plurality; at least 96%; at least 97%; at least 98%; or at least 99% of the overall population of solid units.

Combinations of the aforementioned populations are also within the scope of exemplary embodiments, e.g., two populations of solid units within a plurality where each population has a unique size which is substantially similar within the population and also contains antibodies or peptides to different molecular targets.

In some embodiments, the uniform, free flowing stable solid units may be combined with other uniform, free flowing, stable solid units of a different composition or molecule that can be combined to produce multiple API final drug products for parenteral or oral administration.

In one embodiment, a plurality of solid units comprising a medicament, such as a protein (e.g., a peptide, an antibody, or a DVD-Ig protein) is prepared by dispensing drops of a solution comprising the medicament into a bath of liquid nitrogen or Freon (or any cryogenic solution). The drops are delivered using any suitable dispensing device and are measured such that the substantially the same volume is delivered with each drop. Drops are repeatedly placed in sequence in the liquid nitrogen or Freon such that a plurality of solid units is obtained. Once place in the cryogenic bath, the droplet solidifies to a frozen solid unit. Barriers may be placed within the bath such that each droplet is isolated from other droplets being frozen. The freezing of the droplet is instantaneous and, thus, is performed using controlled nucleation in order to provide consistency among the population of solid units being prepared. If liquid nitrogen is used as the cryogenic agent, once the droplet of solution is frozen, the solid unit generally falls below the surface of the liquid to the bottom of the container. The population of solid units can then be collected and separated from the liquid nitrogen or Freon. The plurality of solid units is next subjected to vacuum sublimation to remove residual water. Following water removal, the plurality of solid units are free-flowing and geometrically uniform in nature. This process may be repeated to obtain a plurality of solid units having different characteristics, e.g., different size or containing a different medicament, where the first batch of solid units can be combined with the second batch to provide a plurality of solid units having distinct features but maintaining the free flowing nature of the units. Further, the aforementioned process may be used to obtain a single solid unit, if desired. This process results in solid units that are spheres due to the freezing step in the liquid nitrogen or Freon, where the solid unit forms in suspension and not on the hard surface of a plate, etc.

In some embodiments, the methods further include contacting a solid unit with a polymer, such as enteric protectant, a slow release polymer, a non-pH sensitive polymer, a solvent, a bioadhesive polymer, or any combination thereof, using methods routine to one of ordinary skill in the art.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step to may be replaced with a plurality of elements or steps that serve the same purpose. Further, where parameters for various properties are specified herein for exemplary embodiments, those parameters may be adjusted up or down by $\frac{1}{20}$th, $\frac{1}{10}^{th}$, $\frac{1}{5}$th, $\frac{1}{3}$rd, $\frac{1}{2}$nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

What is claimed is:

1. A system for administering a final medicament to a patient, the system comprising:
    a first container holding a bulk intermediate medicament;
    a second container holding a diluent to be mixed with the bulk intermediate medicament to form the final medicament;
    a mixing mechanism including a mixing container for mixing the bulk intermediate medicament and the diluent in the mixing container to form the final medicament prior to injection; and
    a wearable automatic injection device separable from the first container, the second container, and the mixing mechanism comprising:
        a housing;
        a port to receive the mixing container containing the final medicament;
        an injection assembly for injecting the patient with the final medicament; and
        an activation mechanism for initiating the injection assembly for administering the final medicament to the patient.

2. The system of claim 1, wherein the mixing mechanism is initiated based on a user actuating a button on the mixing mechanism.

3. The system of claim 1, wherein the mixing mechanism is initiated based on a user actuating a wireless remote in wireless communication with the mixing mechanism.

4. The system of claim 1, further comprising a turbidity meter disposed in the mixing mechanism to automatically verify mixing of the bulk intermediate medicament and diluent.

5. The system of claim 1, further comprising a piezoelectric element coupled to the mixing container and energized by the mixing mechanism when the mixing mechanism is initiated, the piezoelectric element configured to cause the diluent to cavitate and mix with the bulk intermediate medicament.

* * * * *